US012342838B2

(12) United States Patent
Johnson et al.

(10) Patent No.: US 12,342,838 B2
(45) Date of Patent: Jul. 1, 2025

(54) METHOD OF REDUCING THE SELF-HEATING PROPENSITY OF BIOMASS

(71) Applicants: DSM IP ASSETS B.V., Heerlen (NL); Evonik Operations GmbH, Essen (DE)

(72) Inventors: Michael Benjamin Johnson, Columbia, MD (US); Shannon Elizabeth Ethier Resop, Columbia, MD (US)

(73) Assignees: DSM IP ASSETS B.V., Heerlen (NL); EVONIK OPERATIONS GMBH, Essen (DE)

(*) Notice: Subject to any disclaimer, the term of this patent is extended or adjusted under 35 U.S.C. 154(b) by 927 days.

(21) Appl. No.: 17/250,625

(22) PCT Filed: Aug. 9, 2019

(86) PCT No.: PCT/US2019/045838
§ 371 (c)(1),
(2) Date: Feb. 12, 2021

(87) PCT Pub. No.: WO2020/036814
PCT Pub. Date: Feb. 20, 2020

(65) Prior Publication Data
US 2021/0321640 A1   Oct. 21, 2021

Related U.S. Application Data

(60) Provisional application No. 62/718,549, filed on Aug. 14, 2018, provisional application No. 62/876,076, filed on Jul. 19, 2019.

(51) Int. Cl.
| | | |
|---|---|---|
| A23K 20/158 | (2016.01) | |
| A23K 10/16 | (2016.01) | |
| A23K 20/163 | (2016.01) | |
| A23K 30/20 | (2016.01) | |
| C12N 1/12 | (2006.01) | |
| C12P 7/6427 | (2022.01) | |
| C12P 7/6432 | (2022.01) | |
| C12P 7/6434 | (2022.01) | |
| C12P 7/6472 | (2022.01) | |

(52) U.S. Cl.
CPC .......... *A23K 20/158* (2016.05); *A23K 10/16* (2016.05); *A23K 20/163* (2016.05); *A23K 30/20* (2016.05); *C12N 1/12* (2013.01); *C12P 7/6427* (2013.01); *C12P 7/6432* (2022.01); *C12P 7/6434* (2022.01); *C12P 7/6472* (2013.01)

(58) Field of Classification Search
None
See application file for complete search history.

(56) References Cited

U.S. PATENT DOCUMENTS

| | | | |
|---|---|---|---|
| 12,203,408 B2 | 1/2025 | Verkoeijen et al. | |
| 2006/0122410 A1 | 6/2006 | Fichtali et al. | |
| 2013/0129902 A1* | 5/2013 | Verkoeijen | A23L 33/115 435/243 |
| 2018/0000130 A1 | 1/2018 | Rakitsky et al. | |

FOREIGN PATENT DOCUMENTS

| | | | |
|---|---|---|---|
| CN | 102665431 | 9/2012 | |
| CN | 104982920 | 10/2015 | |
| GB | 2437909 | 11/2007 | |
| JP | 2013-509860 | 3/2021 | |
| WO | WO 91/07498 | 5/1991 | |
| WO | WO 2011/054800 | 5/2011 | |
| WO | WO 2015/095690 | 6/2015 | |
| WO | WO-2018005856 A1* | 1/2018 | ............ A23K 10/00 |
| WO | 2019069849 A1 | 4/2019 | |
| WO | WO 2019/122031 | 6/2019 | |
| WO | WO 2019/185888 | 10/2019 | |

OTHER PUBLICATIONS

International Search Report issued by the International Searching Authority in International Application No. PCT/US2019/045838, dated Oct. 17, 2019 (3 pages).
Written Opinion issued by the International Searching Authority in International Application No. PCT/US2019/045838, dated Oct. 17, 2019 (11 pages).
Andrianus J. de Koning, "The Antioxidant Ethoxyquin And Its Analogues: A Review", International Journal of Food Properties, 5:2, 451-461 (2002).

* cited by examiner

*Primary Examiner* — Christian L Fronda
(74) *Attorney, Agent, or Firm* — Nixon & Vanderhye P.C.

(57) ABSTRACT

The present invention discloses a LC-PUFA biomass composition which has reduced self-heating propensity and thus requires a lessened packing requirement for shipment. The invention also discloses methods for making such biomass composition.

9 Claims, 26 Drawing Sheets

METHOD OF REDUCING THE SELF-HEATING PROPENSITY OF BIOMASS

CROSS REFERENCE TO RELATED APPLICATIONS

This application claims the benefit of the filing date of United States Provisional Patent Application Nos. 62/718,549 filed Aug. 14, 2018 and 62/876,076 filed Jul. 19, 2019, the disclosures of which are hereby incorporated herein by reference.

FIELD OF INVENTION

The present invention relates to a method of reducing the self-heating propensity of a biomass which contains significant amount of polyunsaturated fatty acids.

BACKGROUND OF THE INVENTION

Polyunsaturated fatty acids (PUFAs) containing lipids are of high interest in the feed, food and pharmaceutical industry. Fatty acids are classified based on the length and saturation characteristics of the carbon chain. Fatty acids are termed short chain, medium chain, or long chain fatty acids based on the number of carbons present in the chain. Fatty acids are termed saturated fatty acids when no double bonds are present between the carbon atoms. Fatty acids are termed unsaturated fatty acids when double bonds are present. Unsaturated long chain fatty acids are monounsaturated when only one double bond is present. Unsaturated long chain fatty acids are polyunsaturated when more than one double bond is present.

PUFAs can be produced by microorganisms in a fermentation process. The biomass of the PUFA-containing microorganism is collected before being processed to extract the PUFA oil contained within. The biomass of the PUFA-containing microorganism can also be used directly as a product, particularly in the feed industry.

It has been found that PUFA-containing compositions are susceptible to self-heating. For example, during storage or transportation, the temperature of the biomass in the container or package can increase spontaneously, some will ultimately result in unexpected explosions and fires.

In order to ensure safety in transportation of combustible materials, such as self-heating biomass, proper packaging is required. One of the widely accepted standard for classifying combustible materials is the United Nations (UN) Classification of Self-Heating Substance. See FIG. 1. In this classification, several self-heating tests are devised. Based on the result of the tests, packaging requirement will be determined. For example, if a biomass substance undergoes dangerous self-heating when it is heated in an oven in a 100 mm sample cube at 100° C. for a 24 hours period, In according to United Nation's standard, such material is recommended to be packaged in Packing Group III material and is classified as self-heating material and in transport hazard class 4.2. In another example, if a biomass substance does not undergo dangerous self-heating when tested in a 25 mm sample cube at 140° C. during a 24 hours period, and it does not undergo dangerous self-heating when tested in a 100 mm sample cube at 120° C. during a 24 hours period, it will be exempted from being labeled as self-heating substance if it is transported in a package of no more than 3 cubic meters in volume. The different packaging requirements are also used as alternative ways for classifying the self-heating propensity of a biomass.

Some attempts have been made in the past to reduce the self-heating propensity of biomass. For example, WO 2011/054800 describes a process in which the moisture of biomass is controlled during the drying step in order to reduce the self-heating propensity of the biomass. WO2018/005856 describes the use of antioxidants to enhance the oxidative stability of algal biomass.

However, self-heating remains as a challenging problem in transportation and storage of biomass which contains high amount of PUFAs. Thus, there is a need to identify new methods which can effectively reduce self-heating in biomass.

BRIEF SUMMARY OF THE INVENTION

The invention now provides a biomass composition which has reduced self-heating propensity. This composition comprises cells containing one or more type of polyunsaturated fatty acid (PUFA) having at least 20 carbon atoms and at least three double bonds, wherein the composition has at least 20 wt % PUFAs, and wherein the composition does not undergo dangerous self-heating when tested in a 100 mm sample cube at 120° C. In the self-heating test, the sample cubes were suspended in an oven and the oven temperature was held at 120° C. for 24 hours. A sample is classified as self-heating material if the sample temperature spontaneously increased 60° C. or more above the oven temperature, which is 180° C.

The invention also provides a composition comprising cells containing one or more type of polyunsaturated fatty acid (PUFA) having at least 20 carbon atoms and at least three double bonds, wherein the composition has at least 20 wt % PUFAs, and wherein the composition does not undergo dangerous self-heating when tested in a 100 mm sample cube at 100° C. In this self-heating test, the sample cubes were suspended in an oven and the oven temperature was held at 100° C. for 24 hours. A sample is classified as self-heating material if the sample temperature spontaneously increased 60° C. or more above the oven temperature, which is 160° C.

The invention further provides a composition comprising cells containing one or more type of polyunsaturated fatty acid (PUFA) having at least 20 carbon atoms and at least three double bonds, wherein the composition has at least 20 wt % PUFAs, and wherein the composition does not undergo dangerous self-heating when tested in a 25 mm sample cube at 140° C. but still undergoes dangerous self-heating when tested in a 100 mm sample cube at 100° C.

The biomass composition according to the invention has the advantage of reduced self-heating propensity and thus can be shipped more safely than the biomass composition which has not been treated by the methods disclosed in the invention. The packing requirement of the biomass composition treated by the methods disclosed in the invention can be reduced one or more levels than the composition without such treatment. A further advantage of the composition of the invention is that the quality of PUFAs contained in the composition does not deteriorate even after treatment. The methods disclosed in the invention does not negatively impact the quality of PUFAs.

BRIEF SUMMARY OF DRAWINGS

In FIGS. 2-25, the righthand side diagram represents an expanded view of the peak areas shown in the left-hand side diagram.

FIG. 3 shows the temperature profiles of samples D1 and D2 in a 100 mm cube tested at 100° C.

FIG. 4 shows the temperature profiles of samples S1-S5 in a 25 mm cube tested at 140° C.

FIG. 5 shows the temperature profiles of samples S1-S5 in a 100 mm cube tested at 120° C.

FIG. 6 shows the temperature profiles of samples D2 and D3 in a 25 mm cube tested at 140° C.

FIG. 7 shows the temperature profiles of samples D2 and D3 in a 100 mm cube tested at 100° C.

FIG. 8 shows the temperature profiles of samples D3 and D4 in a 25 mm cube tested at 140° C.

FIG. 9 shows the temperature profiles of samples D3 and D4 in a 100 mm cube tested at 100° C.

FIG. 10 shows the temperature profiles of samples D4 and D5 in a 25 mm cube tested at 140° C.

FIG. 11 shows the temperature profiles of samples D4 and D5 in a 100 mm cube tested at 100° C.

FIG. 12 shows the temperature profiles of samples D5 and D6 in a 25 mm cube tested at 140° C.

FIG. 13 shows the temperature profiles of samples D5 and D6 in a 100 mm cube tested at 120° C.

FIG. 14 shows the temperature profiles of samples D4 and D7 in a 25 mm cube tested at 140° C.

FIG. 15 shows the temperature profiles of samples D4 and D7 in a 100 mm cube tested at 100° C.

FIG. 16 shows the temperature profiles of samples D7 and D8 in a 25 mm cube tested at 140° C.

FIG. 17 shows the temperature profiles of samples D7 and D8 in a 100 mm cube tested at 120° C.

FIG. 18 shows the temperature profiles of samples D8 and D9 in a 25 mm cube tested at 140° C.

FIG. 19 shows the temperature profiles of samples D8 and D9 in a 100 mm cube tested at 120° C.

FIG. 20 shows the temperature profiles of samples D9 and D10 in a 25 mm cube tested at 140° C.

FIG. 21 shows the temperature profiles of samples D9 and D10 in a 100 mm cube tested at 120° C.

FIG. 22 shows the temperature profiles of samples D4 and D11 in a 25 mm cube tested at 140° C.

FIG. 23 shows the temperature profiles of samples D4 and D11 in a 100 mm cube tested at 100° C.

FIG. 24 shows the temperature profiles of samples S6-S9 in a 25 mm cube tested at 140° C.

FIG. 25 shows the temperature profiles of samples S6-S9 in a 100 mm cube tested at 100° C.

DETAILED DESCRIPTION OF THE INVENTION

Dried PUFA-containing oleaginous biomass is known to undergo oxidization and can self-heat spontaneously. Such self-heating problem is especially significant in microbial cells which contains long chain polyunsaturated fatty acids (LC-PUFA). In order to identify means to reduce the self-heating propensity of biomass, different conditions were examined via experiments, such as length of fermentation, pasteurization, drying method, addition of inert ingredient, and addition of antioxidants. Table 1 shows a chart of samples prepared and tested in the present application.

TABLE 1

| Sample | Culture Age (Days) | Pasteurized? | Drying Method | Additions |
|---|---|---|---|---|
| D1 | 2 | No | Lyophilization | None |
| D2 | 6 | No | Lyophilization | None |
| D3 | 6 | Yes | Lyophilization | None |
| D4 | 6 | Yes | Drum Drying | None |
| D5 | 6 | Yes | Drum Drying | 2000 ppm ethoxyquin |
| D6 | 6 | Yes | Drum Drying | 2000 ppm ethoxyquin, 1% lecithin |
| D7 | 6 | Yes | Drum Drying | 2% Roseen |
| D8 | 6 | Yes | Drum Drying | 2% Roseen, 1% lecithin |
| D9 | 6 | Yes | Drum Drying | 2% Roseen, 1% lecithin, 4000 ppm TAP1010 |
| D10 | 6 | Yes | Drum Drying | 2% Roseen, 1% lecithin, 4000 ppm TAP1010, 300 ppm TBHQ |
| D11 | 6 | Yes | Drum Drying | 50 g/L dextrose |
| S1 | 2 | No | Lyophilization | None |
| S2 | 3 | No | Lyophilization | None |
| S3 | 4 | No | Lyophilization | None |
| S4 | 5 | No | Lyophilization | None |
| S5 | 6 | No | Lyophilization | None |
| S6 | 6 | Yes | Lyophilization | None |
| S7 | 6 | Yes | Lyophilization | 50 g/L fructose |
| S8 | 6 | Yes | Lyophilization | 50 g/L sucrose |
| S9 | 6 | Yes | Lyophilization | 50 g/L maltose |

Figure 1:
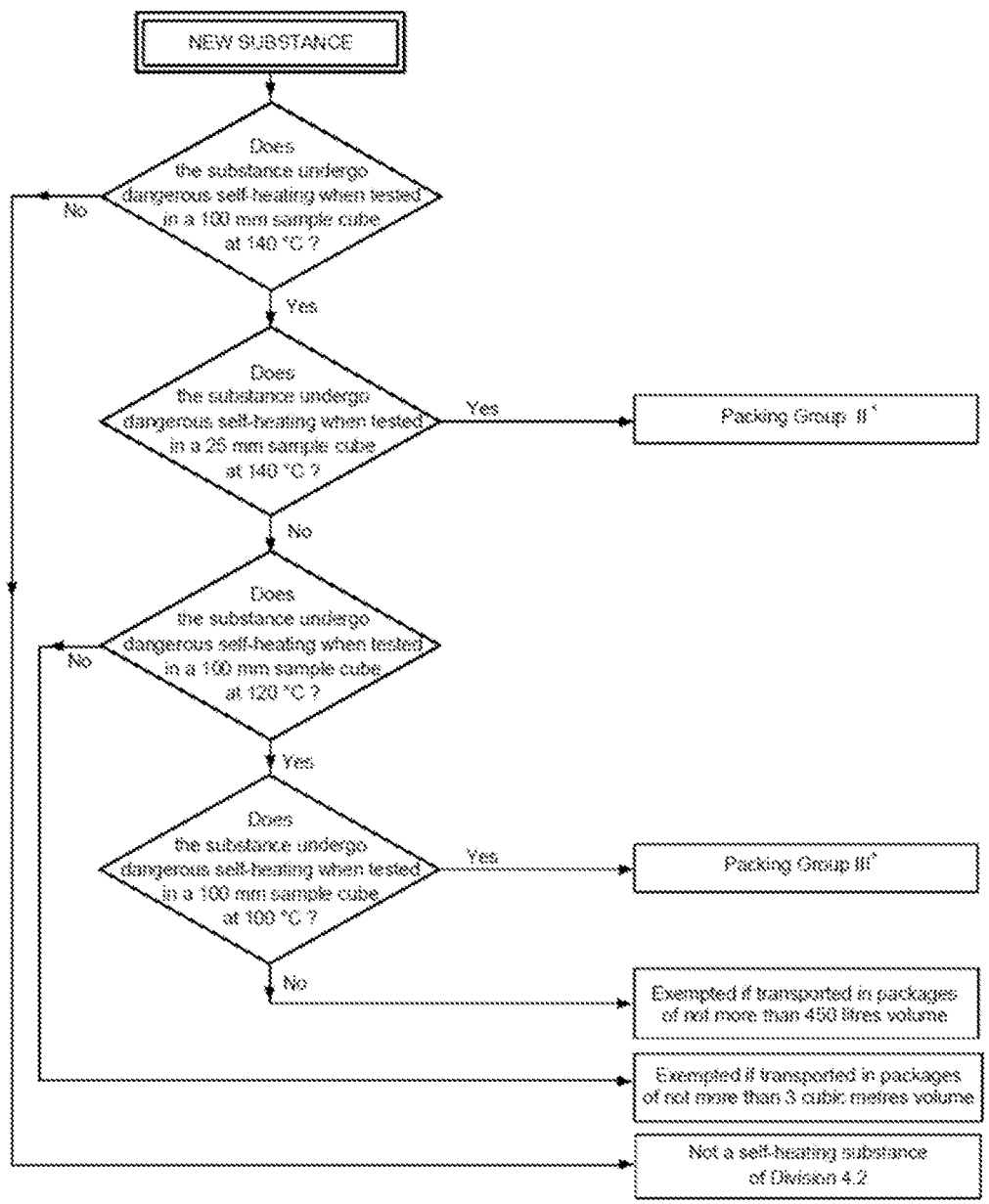
FIG. 1 is a diagram illustrating the UN classification of self-heating substances.

The samples were tested using the United Nations 49 CFR 173.124—Class 4, Division 4.2 classification of self-heating substances (see FIG. 1). In the self-heating test, the sample cubes were suspended in an oven and the oven temperature was held at the given temperature for 24 hours. A sample is considered as undergoing dangerous self-heating if the sample temperature spontaneously increased 60° C. or more above the ambient internal temperature (set point) of the oven. Tests were performed in 25 mm and 100 mm cubes at temperatures ranging from 100-140° C. A series tests are conducted in order to determine the classification of any given self-heating substance. For example, if the substance does not undergo dangerous self-heating as defined above when tested in a 100 mm sample cube at 140° C., the substance is considered non-self-heating substance of Division 4.2 of the UN standard. If the substance does self-heat at the above condition, a further test in a 25 mm sample cube at 140° C. will be conducted. If the substance self-heat under the new condition, it will be classified under UN standard Division 4.2 as dangerous self-heating material which requires Packing Group II packing material when in transportation. In the present invention. the corresponding samples were compared and analyzed based on temperature profiles as shown in FIG. 1 to determine if reduction in oxidation and self-heating characteristics were obtained.

It was known that the susceptibility of a biomass increases with higher PUFA content. In particular, PUFAs with 20 or more carbon atoms have higher susceptibility to self-heating. It is also known that the susceptibility of a biomass increases with higher number of double bonds of the PUFAs. In particular, PUFAs with 3 or more double bonds have higher susceptibility to self-heating.

It has been identified in this invention that reduction of length of fermentation, elimination of pasteurization step (batch or in-line after the fermentation), changing drying method, addition of inert ingredient, and addition of antioxidant will help reducing the susceptibility of biomass to self-heating.

By employing one or more of the above methods, a biomass composition with reduced self-heating propensity was produced.

In one embodiment, the invention provides a composition comprising cells containing one or more type of polyunsaturated fatty acid (PUFA) having at least 20 carbon atoms and at least three double bonds, wherein the composition has at least 20 wt % PUFAs, and wherein the composition does not spontaneously self-heat in a test oven, i.e., defined as that the composition's temperature is not increased 60° C. or more above the oven temperature of 120° C. when the composition is placed in a 100 mm sample cube and heated in an oven at 120° C. for 24 hours. In one embodiment, the above composition further comprises an effective amount of at least one added antioxidant to provide oxidative stability.

The composition that falls into the above description can be classified as exempted substance if it is transported in packages of not more than 3 cubic meters volume based on the United Nations 49 CFR 173.124—Class 4, Division 4.2 classification. See FIG. 1.

In one embodiment, the invention provides a composition comprising cells containing one or more type of polyunsaturated fatty acid (PUFA) having at least 20 carbon atoms and at least three double bonds, wherein the composition has at least 20 wt % PUFAs, and the composition is classified as exempted substance when it is transported in packages of not more than 3 cubic meters in volume based on the United Nations 49 CFR 173.124—Class 4, Division 4.2 classification. In one embodiment, the above composition further comprises an effective amount of at least one added antioxidant to provide oxidative stability.

In another embodiment, the invention provides a composition comprising cells containing one or more type of polyunsaturated fatty acid (PUFA) having at least 20 carbon atoms and at least three double bonds, wherein the composition does not spontaneously self-heat in a test oven, i.e., defined as that the composition's temperature is not increased 60° C. or more above the oven temperature of 100° C. when the composition is placed in a 100 mm sample cube and heated in an oven at 100° C. for 24 hours. In one embodiment, the above composition further comprises an effective amount of at least one added antioxidant to provide oxidative stability.

The composition that falls into the above description can be classified as exempted substance if it is transported in packages of not more than 450 liters volume based on the United Nations 49 CFR 173.124—Class 4, Division 4.2 classification. See FIG. 1.

In one embodiment, the invention provides a composition comprising cells containing one or more type of polyunsaturated fatty acid (PUFA) having at least 20 carbon atoms and at least three double bonds, wherein the composition has at least 20 wt % PUFAs, and the composition is classified as exempted substance when it is transported in packages of not more than 450 liters in volume based on the United Nations 49 CFR 173.124—Class 4, Division 4.2 classification. In one embodiment, the above composition further comprises an effective amount of at least one added antioxidant to provide oxidative stability.

In another embodiment, the invention provides a composition comprising cells containing one or more type of polyunsaturated fatty acid (PUFA) having at least 20 carbon atoms and at least three double bonds, wherein the composition has at least 20 wt % PUFAs, and wherein the composition does not spontaneously self-heat in a test oven, i.e., defined as that the composition's temperature is not increased 60° C. or more above the oven temperature of 140° C. when the composition is placed in a 25 mm sample cube and heated in an oven at 140° C. for 24 hours, but the composition still undergoes dangerous self-heating in a test oven, i.e., defined as that the composition's temperature is increased 60° C. or more above the oven temperature of 100° C. when the composition is placed in a 100 mm sample cube and is heated in the oven at 100° C. for 24 hours. In one embodiment, the above composition further comprises an effective amount of at least one added antioxidant to provide oxidative stability.

The composition that falls into the above description can avoid Packing Group II label requirement but is still required to use Packing Group III packing materials and labeled as such in accordance with the United Nations 49 CFR 173.124—Class 4, Division 4.2 classification. See FIG. 1.

In one embodiment, the invention provides a composition comprising cells containing one or more type of polyunsaturated fatty acid (PUFA) having at least 20 carbon atoms and at least three double bonds, wherein the composition has at least 20 wt % PUFAs, and the composition is not required to have Packing Group II label requirement based on the United Nations 49 CFR 173.124—Class 4, Division 4.2 classification.

In one embodiment, the invention provides a composition comprising cells containing one or more type of polyunsaturated fatty acid (PUFA) having at least 20 carbon atoms and at least three double bonds, wherein the composition has at least 20 wt % PUFAs, and the composition is only required to have Packing Group III label requirement based on the United Nations 49 CFR 173.124—Class 4, Division 4.2 classification.

The composition having the reduced self-heating propensity as recited above can be obtained based on the teachings provided by the present invention as described below.

It is found that the self-heating propensity of a biomass can be reduced by harvesting cells from fermentation broth earlier than normal to obtain young cells. In one embodiment, the self-heating propensity of a biomass can be reduced if the fermentation process is ended before day 5 of the fermentation. In one embodiment, the self-heating propensity of a biomass can be reduced if the fermentation process is ended before day 6 of the fermentation. In one embodiment, the self-heating propensity of a biomass can be reduced if the fermentation process is ended before day 7 of the fermentation.

It is also found that the self-heating propensity of a biomass can be reduced if it is dried by a drum drying method instead of a lyophilization method.

It is also found that the self-heating propensity of a biomass can be reduced by adding two different types of antioxidants. The reduction of self-heating propensity of a biomass is surprisingly good if a natural antioxidant is used in combination with a synthetic antioxidant. In one embodiment, the natural antioxidant may be either lecithin or Roseen. In another embodiment, synthetic antioxidant may be one of ethoxyquin, TAP1010 or TBHQ.

It is also found that the self-heating propensity of a biomass can be reduced by adding inert ingredients to dried biomass. It has been discovered that addition of sugar to fermentation broth after the broth is pasteurized can help reduce the self-heating propensity of biomass. In one embodiment, the inert ingredient can be any composition that is not reactive with cell biomass. In a specific embodiment, the inert ingredient is sugar. In one embodiment, the sugar may be selected from a group consisting of dextrose, fructose, sucrose, and maltose. The same effect can be achieved through ending the fermentation before the sugar source is fully consumed by the microorganism, such as in the earlier harvest examples previously mentioned.

In one embodiment, the self-heating propensity of a biomass can be further reduced if treated in a process which combines any two or more of the above described methods.

In a preferred embodiment, the composition according to the invention has an oil content and PUFA as described below.

The biomass composition of the invention has self-heating propensity before treatment because it contains a reasonable level of polyunsaturated fatty acids. In one embodiment, the composition comprises an oil which comprises at least 20 wt. %, for instance at least 25 wt. %, for instance at least 30 wt. %, for instance at least 35 wt. %, for instance at least 40 wt. %, for instance at least 45 wt. %, for instance at least 50 wt. %, for instance at least 55 wt. %, for instance at least 60 wt. %, for instance at least 65 wt. %, for instance at least 70 wt. %, for instance at least 75 wt. %, for instance at least 80 wt. %, for instance at least 90 wt. %, for instance at least 95 wt. % of the weight of the composition. In another embodiment, the composition comprises an oil which comprises between 30-70 wt. %, for instance between 40-60 wt. %, for between 45-55 wt. % of the weight of the composition. In one embodiment, the weight of the composition is referred to as the dry cell weight of a biomass. Such biomass can be algal cells or any other PUFA-containing microbial cells.

In an embodiment of the invention, the composition comprises PUFA, specially LC-PUFA. In one embodiment, the composition is a biomass. In another embodiment, the composition is a dried biomass. In another embodiment, the composition is the dried biomass of microbial cells. In another embodiment, the composition is the dried biomass of algal cells.

In one embodiment, the composition comprises at least 20 wt. %, for instance at least 25 wt. %, at least 30 wt. %, at least 35 wt. %, at least 40 wt. %, at least 45 wt. %, at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, at least 95 wt. %, at least 100 wt. % PUFA with at least 3 double bonds with respect to the total fatty acids in the oil. In one embodiment, the weight of the composition is referred to as the dry cell weight of a biomass.

In one embodiment, the composition comprises at least 20 wt. %, for instance at least 25 wt. %, at least 30 wt. %, at least 35 wt. %, at least 40 wt. %, at least 45 wt. %, at least 50 wt. %, at least 55 wt. % PUFAs with at least 3 double bonds with respect to the weight of said composition. In another embodiment, the composition comprises between 20-55 wt. %, between 20-40 wt. %, between 20-30 wt. %, or 20-25 wt. % PUFAs with at least 3 double bonds with respect to the weight of said composition. In one embodiment, the weight of the composition is referred to as the dry cell weight of a biomass.

In one embodiment, the invention is directed to a method for lowering the self-heating propensity of a composition comprising cells containing one or more polyunsaturated fatty acid (PUFA) having at least 20 carbon atoms and at least three double bonds, wherein the composition has at least 20 wt % PUFAs, and wherein the method comprising limiting the length of fermentation process to less than 6 days.

In one embodiment, the invention is directed to a method for lowering the self-heating propensity of a composition comprising cells containing one or more polyunsaturated fatty acid (PUFA) having at least 20 carbon atoms and at least three double bonds, wherein the composition has at least 20 wt % PUFAs, and wherein the method comprising removing the pasteurization step after fermentation.

In one embodiment, the invention is directed to a method for lowering the self-heating propensity of a composition comprising cells containing one or more polyunsaturated fatty acid (PUFA) having at least 20 carbon atoms and at least three double bonds, wherein the composition has has at least 20 wt % PUFAs, and wherein the method comprising a drum drying step instead of a lyophilization step.

In one embodiment, the invention is directed to a method for lowering the self-heating propensity of a composition comprising cells containing one or more polyunsaturated fatty acid (PUFA) having at least 20 carbon atoms and at least three double bonds, wherein the composition has at least 20 wt % PUFAs, and wherein the method comprising adding at least one type of natural antioxidant and at least on type of synthetic antioxidant to a fermentation broth at the end of fermentation.

In one embodiment, the natural antioxidant is lecithin or Roseen, and wherein said synthetic antioxidant is ethoxyquin, TAP1010 or TBHQ.

In one embodiment, the invention is directed to a method for lowering the self-heating propensity of a composition comprising cells containing one or more polyunsaturated fatty acid (PUFA) having at least 20 carbon atoms and at least three double bonds, wherein the composition has at least 20 wt % PUFAs, and wherein the method comprising including at least 50 g/L sugar to a fermentation broth at the end of fermentation.

In one embodiment, the sugar is one or more type selected from a group consisting of: dextrose, fructose, sucrose, and maltose.

In one embodiment, the composition which is recited in the above methods comprises at least 20 wt. %, for instance at least 25 wt. %, at least 30 wt. %, at least 35 wt. %, at least 40 wt. %, at least 45 wt. %, at least 50 wt. %, at least 55 wt. % PUFAs with at least 3 double bonds with respect to the weight of said composition. In another embodiment, the composition comprises between 20-55 wt. %, between 20-40 wt. %, between 20-30 wt. %, or 20-25 wt. % PUFAs with at least 3 double bonds with respect to the weight of said composition. In one embodiment, the weight of the composition is referred to as the dry cell weight of a biomass.

In one embodiment, the weight of the composition is referred to as the dry cell weight of a biomass. Such biomass can be algal cells or any other PUFA-containing microbial cells.

In an embodiment of the invention, the composition which is recited in the above methods comprises PUFA, specially LC-PUFA. In one embodiment, the composition is a biomass. In another embodiment, the composition is a dried biomass. In another embodiment, the composition is the dried biomass of microbial cells. In another embodiment, the composition is the dried biomass of algal cells.

In one embodiment, the composition is biomass. In another embodiment, the biomass are microbial cells. The microbial cells may be of the genus *Mortierella, Schizochytrium, Thraustochytrium*, or *Crypthecodinium*.

In one embodiment, the above described PUFAs is one or more type of long chain PUFAs. In another embodiment, the above described PUFAs is an co-3 or an co-6 PUFA. In another embodiment, the above described PUFAs is one or more PUFA selected from selected from dihomo-γ-linolenic acid (DGLA, 20:3 ω-6), arachidonic acid (ARA, 20:4 ω-6), eicosapentaenoic acid (EPA, 20:5 docosahexaenoic acid (DHA: 22:6 ω-3), docosapentaenoic acid (DPA 22:5 ω-3, or DPA 22:5, ω-6).

LC-PUFAs described in this application are fatty acids that contain at least 3 double bonds and have a chain length of 20 or more carbons. Polyunsaturated fatty acids (PUFAs) are classified based on the position of the first double bond from the methyl end of the fatty acid; omega-3 (n-3) fatty acids contain a first double bond at the third carbon, while omega-6 (n-6) fatty acids contain a first double bond at the sixth carbon. For example, docosahexaenoic acid (DHA) is an omega-3 long chain polyunsaturated fatty acid (LC-PUFA) with a chain length of 22 carbons and 6 double bonds, often designated as "22:6n-3." In one embodiment, the PUFA is selected from an omega-3 fatty acid, an omega-6 fatty acid, and mixtures thereof. In another embodiment, the PUFA is selected from LC-PUFAs. In a still further embodiment, the PUFA is selected from docosahexaenoic acid (DHA), eicosapentaenoic acid (EPA), docosapentaenoic acid (DPA), arachidonic acid (ARA), gamma-linolenic acid (GLA), dihomo-gamma-linolenic acid (DGLA), stearidonic acid (SDA), and mixtures thereof. In another embodiment, the PUFA is selected from DHA, ARA, and mixtures thereof. In a further embodiment, the PUFA is DHA. In yet a further embodiment, the PUFA is ARA.

As used herein, a "cell" refers to an oil-containing biomaterial, such as biomaterial derived from oleaginous microorganisms. Oil produced by a microorganism or obtained from a microbial cell is referred to as "microbial oil". In one embodiment, microbial oil refers to a crude oil extracted from the biomass of the microorganism without further processing. Oil produced by algae and/or fungi is also referred to as algal and/or fungal oil, respectively.

As used herein, a "microorganism" refers to organisms such as algae, bacteria, fungi, yeast, protist, and combinations thereof, e.g., unicellular organisms. In some embodiments, a microbial cell is a eukaryotic cell. A microbial cell includes, but is not limited to, golden algae (e.g., microorganisms of the kingdom Stramenopiles); green algae; diatoms; dinoflagellates (e.g., microorganisms of the order Dinophyceae including members of the genus Crypthecodinium such as, for example, Crypthecodinium cohnii or C. cohnii); microalgae of the order Thraustochytriales; yeast (Ascomycetes or Basidiomycetes); and fungi of the genera Mucor, Mortierella, including but not limited to Mortierella alpina and Mortierella sect, schmuckeri, and Pythium, including but not limited to Pythium insidiosum.

In one embodiment, the microorganisms are from the genus Mortierella, genus Crypthecodinium, or order Thraustochytriales. In a still further embodiment, the microbial cells are from Crypthecodinium cohnii. In yet an even further embodiment, the microbial cells are selected from Crypthecodinium cohnii, Mortierella alpina, genus Thraustochytrium, genus Schizochytrium, and mixtures thereof.

In a still further embodiment, the microorganisms include, but are not limited to, microorganisms belonging to the genus Mortierella, genus Conidiobolus, genus Pythium, genus Phytophthora, genus Penicillium, genus Cladosporium, genus Mucor, genus Fusarium, genus Aspergillus, genus Rhodotorula, genus Entomophthora, genus Echinosporangium, and genus Saprolegnia. In another embodiment, ARA is obtained from microbial cells from the genus Mortierella, which includes, but is not limited to, Mortierella elongata, Mortierella exigua, Mortierella hygrophila, Mortierella alpina, Mortierella schmuckeri, and Mortierella minutissima. In a still further embodiment, the microbial cells are from Mortierella alpina.

In an even further embodiment, the microbial cells are from microalgae of the order Thraustochytriales, which includes, but is not limited to, the genera Thraustochytrium (species include arudimentale, aureum, benthicola, globosum, kinnei, motivum, multirudimentale, pachydermum, proliferum, roseum, striatum); the genera Schizochytrium (species include aggregatum, limnaceum, mangrovei, minutum, octosporum); the genera Ulkenia (species include amoeboidea, kerguelensis, minuta, profunda, radiate, sailens, sarkariana, schizochytrops, visurgensis, yorkensis); the genera Aurantiacochytrium; the genera Oblongichytrium; the genera Sicyoidochytrium; the genera Parientichytrium; the genera Botryochytrium; and combinations thereof. In another embodiment, the microbial cells are from the order Thraustochytriales. In yet another embodiment, the microbial cells are from Thraustochytrium. In still a further embodiment, the microbial cells are from Schizochytrium. In a still further embodiment, the microbial cells are chosen from genus Thraustochytrium, Schizochytrium, or mixtures thereof.

EXAMPLES

Example 1

Figure 2:
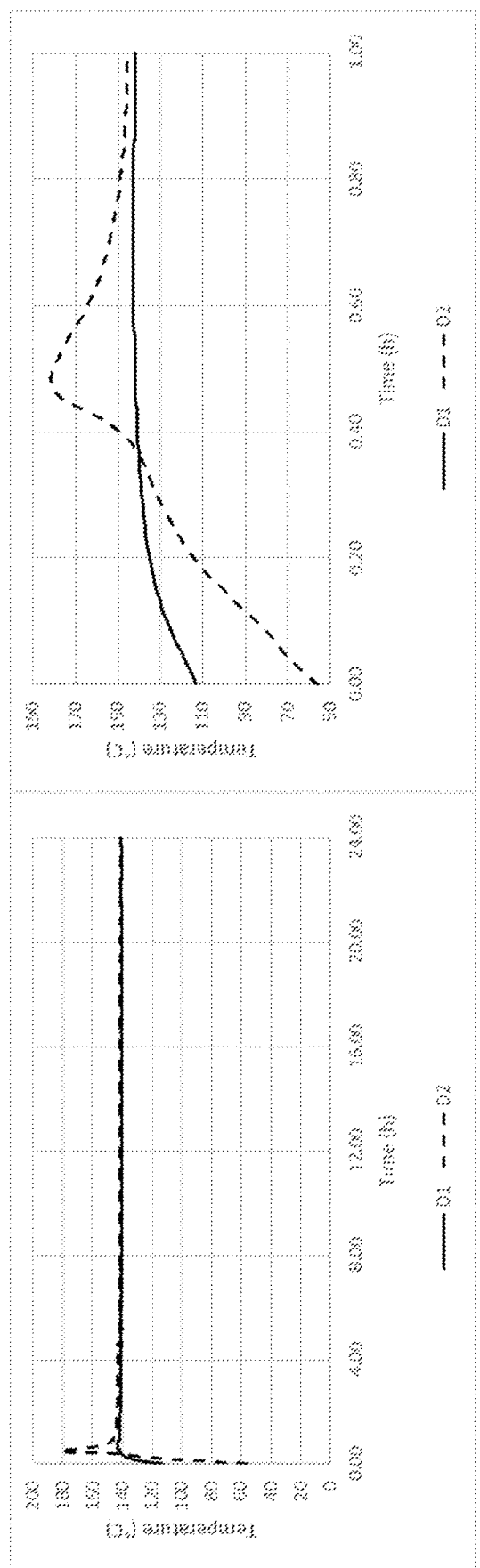
FIG. 2 shows the temperature profiles of samples D1 and D2 in a 25 mm cube tested at 140° C.
Figure 3:
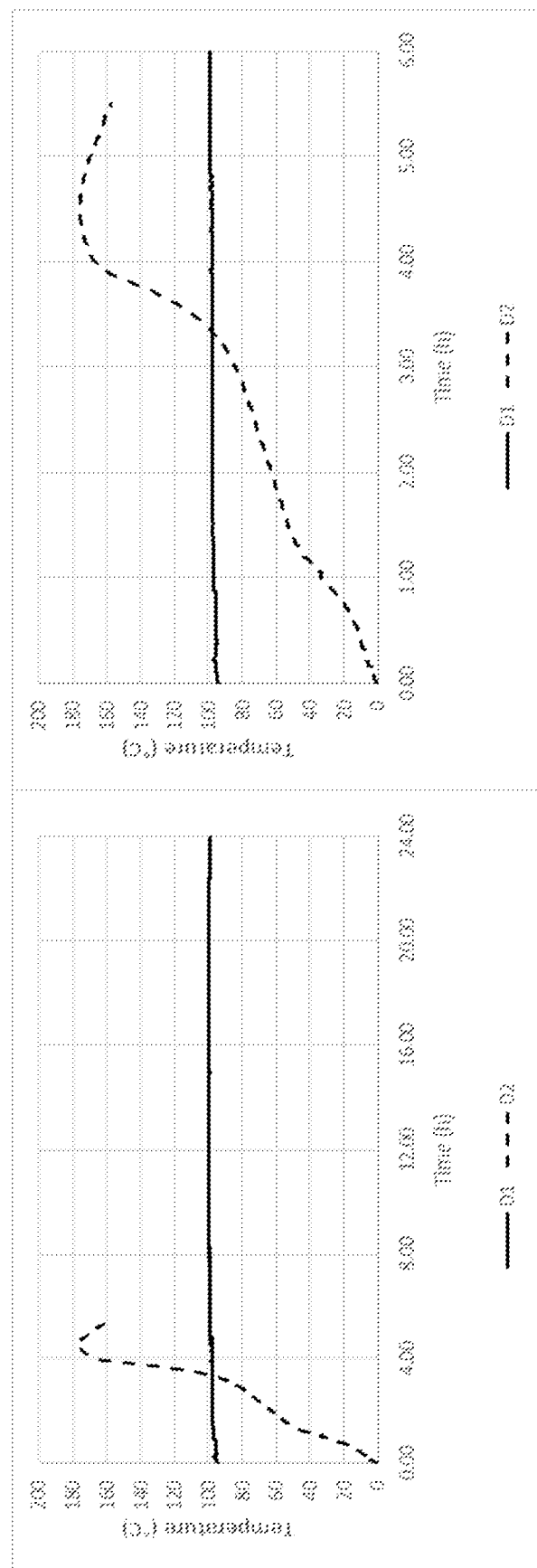

In this example, Schizochytrium sp. was cultivated in fermentation vessels. Harvesting fermentation broth early to obtain younger cells (D1) eliminated the self-heating characteristic when compared to harvesting broth at the end of fermentation (D2). Both samples were dried via lyophilization. See Table 2. Two tests were performed on each of these two samples: 25 mm cube at 140° C., and 100 mm cube at 100° C. The temperature profile for each test can be seen FIG. 2 and FIG. 3. Self-heating is clearly seen in D2 where the temperature increased >60° C. above the oven temperature setpoint, while no self-heating was observed in D1: the sample temperature never increased above the oven temperature when both are compared using the 100 mm cube at 100° C. Therefore, D2 would be classified in Packing Group III, and D1 would not according to FIG. 1.

TABLE 2

| Sample | Culture Age (Days) | Pasteurized? | Drying Method | Fat % | PUFA % |
|---|---|---|---|---|---|
| D1 | 2 | No | Lyophilization | 72.7% | 44.1% |
| D2 | 6 | No | Lyophilization | 51.3% | 46.8% |
| S1 | 2 | No | Lyophilization | 14.1% | 49.6% |
| S2 | 3 | No | Lyophilization | 14.9% | 45.0% |
| S3 | 4 | No | Lyophilization | 26.6% | 42.1% |
| S4 | 5 | No | Lyophilization | 41.3% | 45.3% |
| S5 | 6 | No | Lyophilization | 47.3% | 45.2% |

Figure 4:
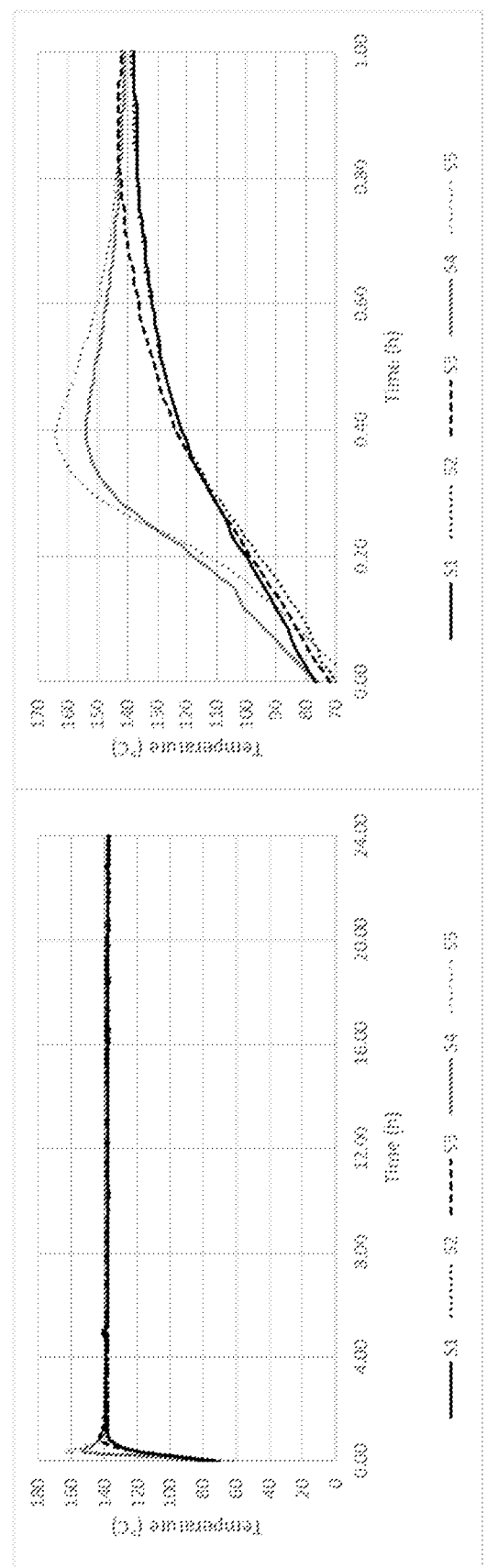
Figure 5:
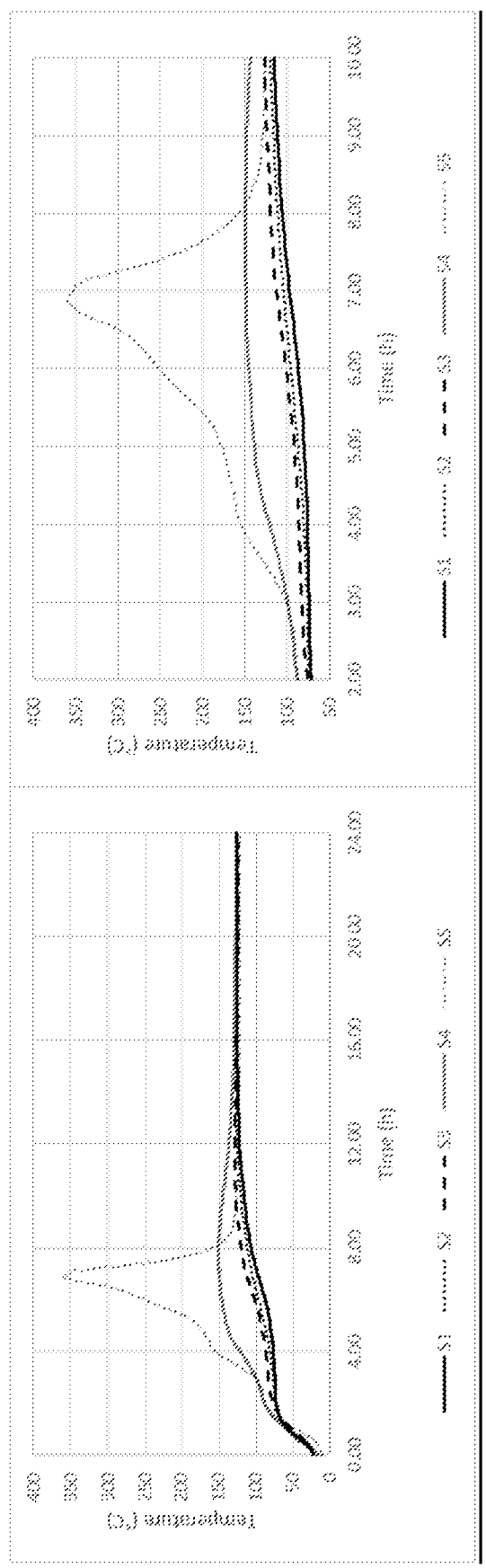

Next, harvesting broth at different time points was tested to determine when self-heating characteristics developed. Samples were tested at the following time points: 2 (S1), 3 (S2), 4 (S3), 5 (S4), and 6 (S5) days. See Table 2. Two tests were performed on each of these two samples: 25 mm cube at 140° C. and 100 mm cube at 120° C. The temperature profiles for these tests can be seen FIG. 4 and FIG. 5. Self-heating is clearly seen in samples S4 and S5 (5 and 6-day fermentation samples respectively). For the 25 mm cube at 140° C., S4 went 14° C. above the setpoint while S5 went 24° C. above the set point. For the 100 mm cube at 120° C., S4 went 30° C. above the setpoint while S5 exhibited dangerous self-heating, reaching a temperature 240° C. above the setpoint. Therefore, ending the fermentation at day 5 can help reduce product self-heating. Sample S1-S4 can be classified as exempt by the UN standard if transported in packages of not more than 3 cubic meters volume.

Example 2

Figure 6:
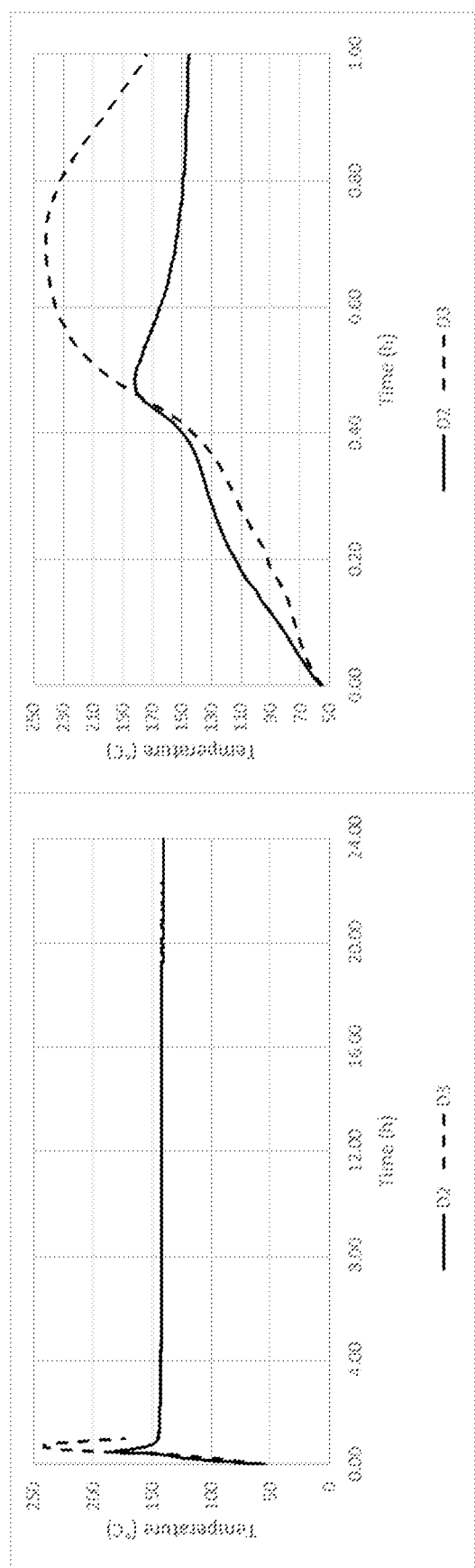
Figure 7:
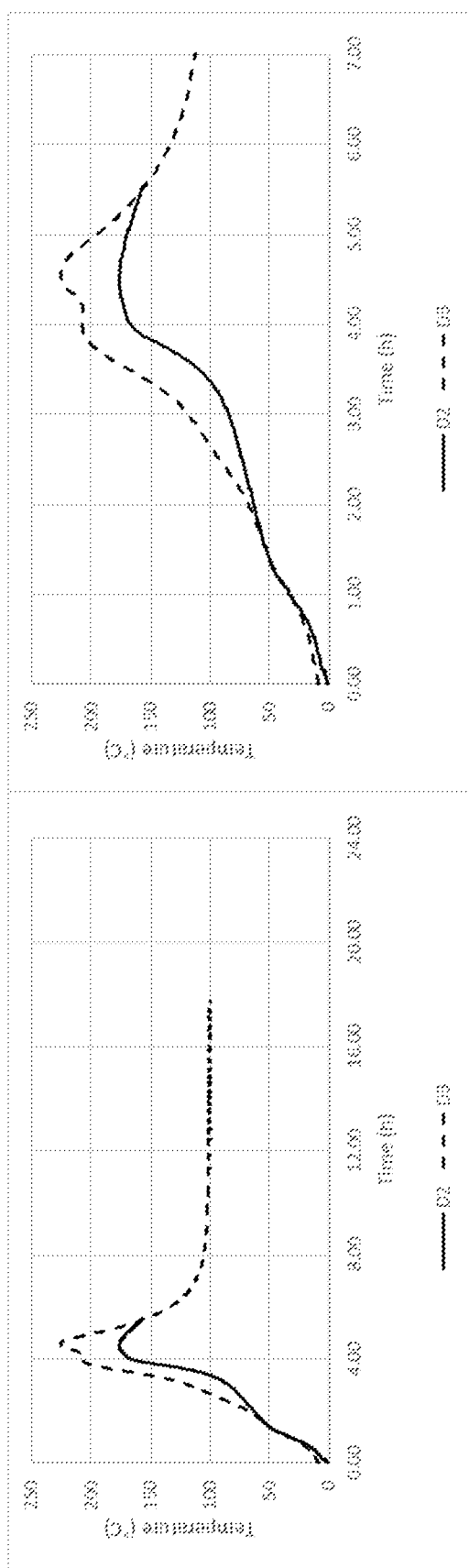

In this example, the same *Schizochytrium* sp. strain as in Example 1 was used. A comparison of unpasteurized vs pasteurized cells showed an unexpected and surprising result. Drying unpasteurized fermentation broth (D2) helped improve self-heating propensity compared to broth that was dried after pasteurization (D3). See Table 3. Both samples were identically dried via lyophilization. Two tests were performed on each sample: 25 mm cube at 140° C. and 100 mm cube at 100° C. The temperature profile for each test can be seen in FIG. 6 and FIG. 7. For the 25 mm cube at 140° C., D3 underwent dangerous self-heating, reaching a maximum temperature 60° C. higher than D2. For the 100 mm cube at 100° C., D3 reached a maximum temperature 50° C. higher than D2, while both increased above the ambient oven temperature. Therefore, according to FIG. 1, D3 would be classified as Packing Group II while D2 would be classified under Packing Group III.

TABLE 3

| Sample | Culture Age (Days) | Pasteurized? | Drying Method | Fat % | PUFA % |
|---|---|---|---|---|---|
| D2 | 6 | No | Lyophilization | 51.3% | 44.1% |
| D3 | 6 | Yes | Lyophilization | 60.4% | 46.8% |

Example 3

Figure 8:
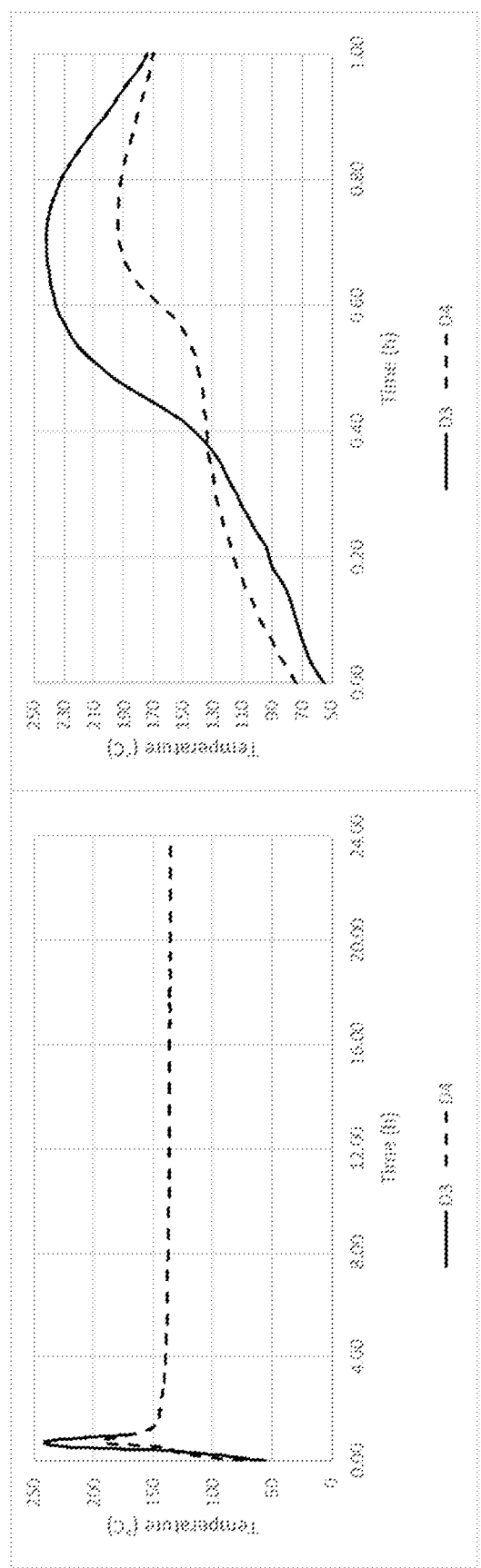
Figure 9:
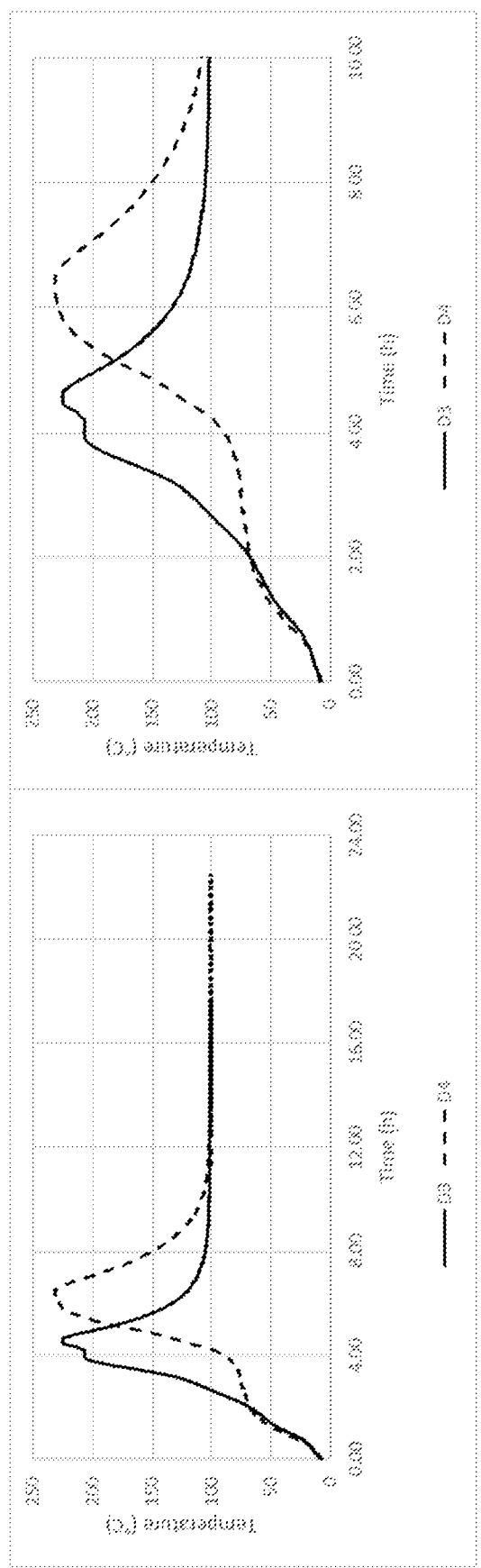

In this example, the same *Schizochytrium* sp. strain as in Example 1 was used. A surprising discovery was made when the drying method was investigated. When whole-cell biomass was dried via rotary drum drying (D4), the self-heating characteristics were improved when compared to whole-cell biomass that was dried via lyophilization (D3). See Table 4. This is surprising when the difference between residual moisture content was insignificant. Two tests were performed on each of these samples: 25 mm cube at 140° C. and 100 mm cube at 100° C. The temperature profile for each test can be seen in FIG. 8 and FIG. 9. For the 25 mm cube at 140° C., the time taken to reach the maximum temperature was about the same for each sample, but the maximum temperature that D4 reached was 48° C. lower than that of D3. For the 100 mm cube at 100° C., the reverse was observed, the maximum temperatures were about the same (~230° C.), but D4 took 1.7 hours longer to reach this temperature than D3. From this data D3 would be classified under Packing Group II while D4 would be classified under Packing Group III (see FIG. 1).

TABLE 4

| Sample | Culture Age (Days) | Pasteurized? | Drying Method | Fat % | PUFA % |
|---|---|---|---|---|---|
| D3 | 6 | Yes | Lyophilization | 50.4% | 46.8% |
| D4 | 6 | Yes | Drum Drying | 50.6% | 48.0% |

Example 4

Figure 10:
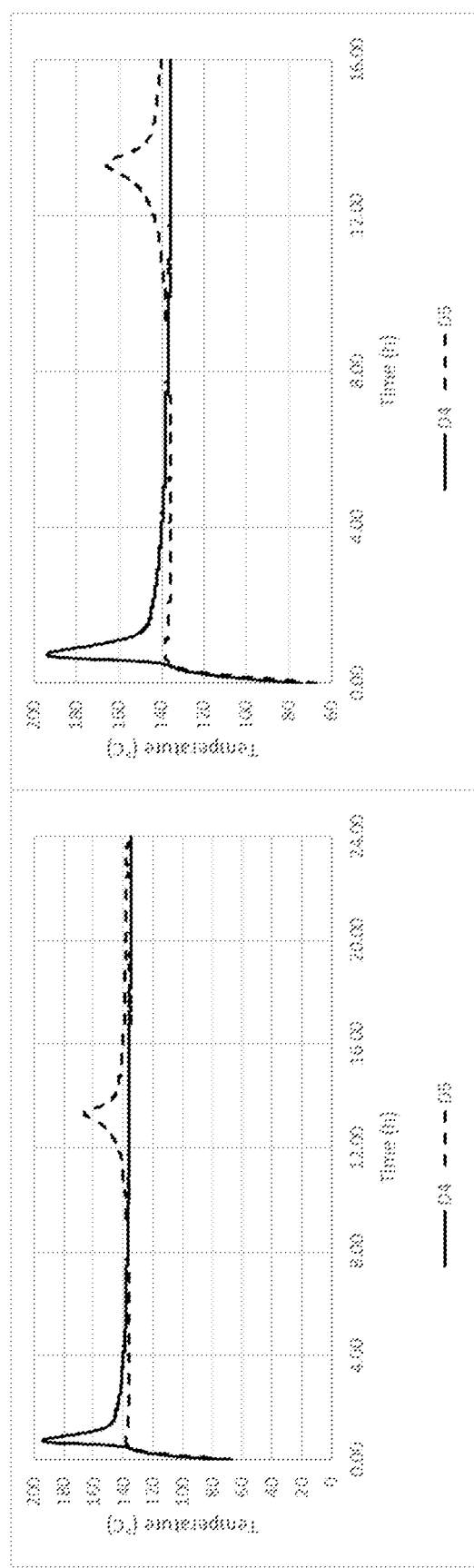
Figure 11:
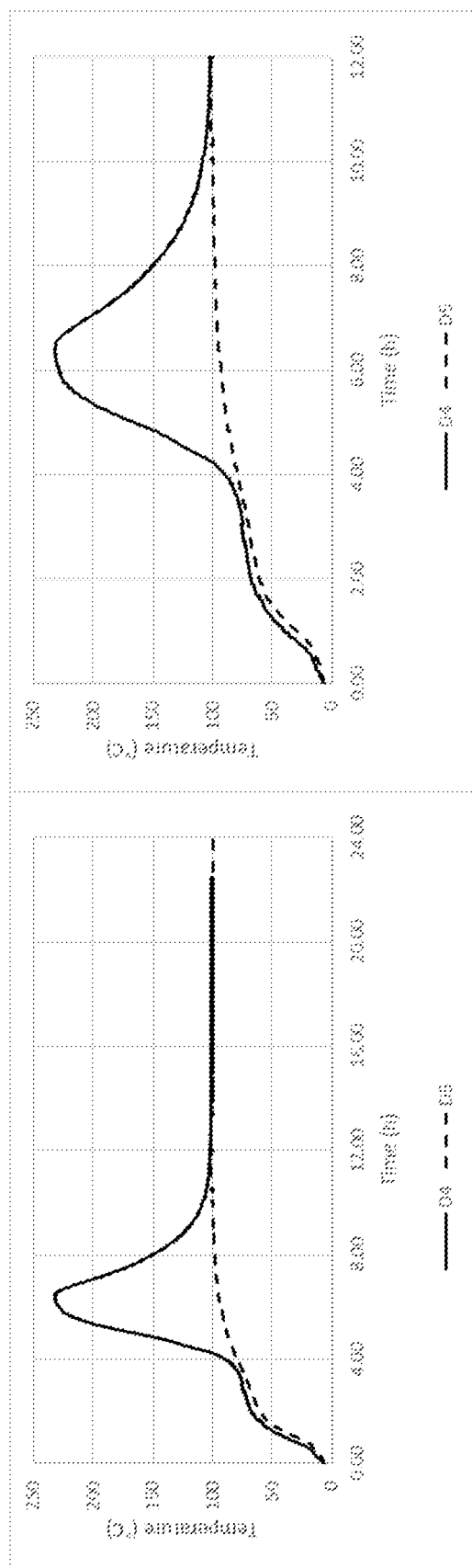

In this example, the same *Schizochytrium* sp. strain as in Example 1 was used. Several different experiments were performed to test the effectiveness of different antioxidants and combinations thereof. Adding the antioxidant ethoxyquin to pasteurized fermentation broth (D5) helped improve self-heating performance when compared to broth with no antioxidant (D4). See Table 5. Later examples show that combinations of antioxidants can have unexpected results. Both samples were dried via drum drying. Two tests were performed on each of these samples: 25 mm cube at 140° C. and 100 mm cube at 100° C. The temperature profile for each test can be seen in FIG. 10 and FIG. 11. For the 25 mm cube at 140° C., the maximum temperature was reduced by 28° C. and the time taken to reach that temperature was increased by 12.5 hours for D5 when compared to D4. For the 100 mm cube at 100° C., D4 underwent dangerous self-heating, while no self-heating was observed in D5. Both results confirm the effectiveness of ethoxyquin in reducing the chance of self-heating. Therefore, D4 would be classified under Packing Group III, and D5 would not be classified under either Packing Group III or Packing Group II according to Figure

TABLE 5

| Sample | Culture Age (Days) | Pasteurized? | Drying Method | Fat % | PUFA % | Additions |
|---|---|---|---|---|---|---|
| D4 | 6 | Yes | Drum Drying | 50.6% | 48.0% | None |
| D5 | 6 | Yes | Drum Drying | 51.2% | 47.3% | 2000 ppm ethoxyquin |

Example 5

Figure 12:
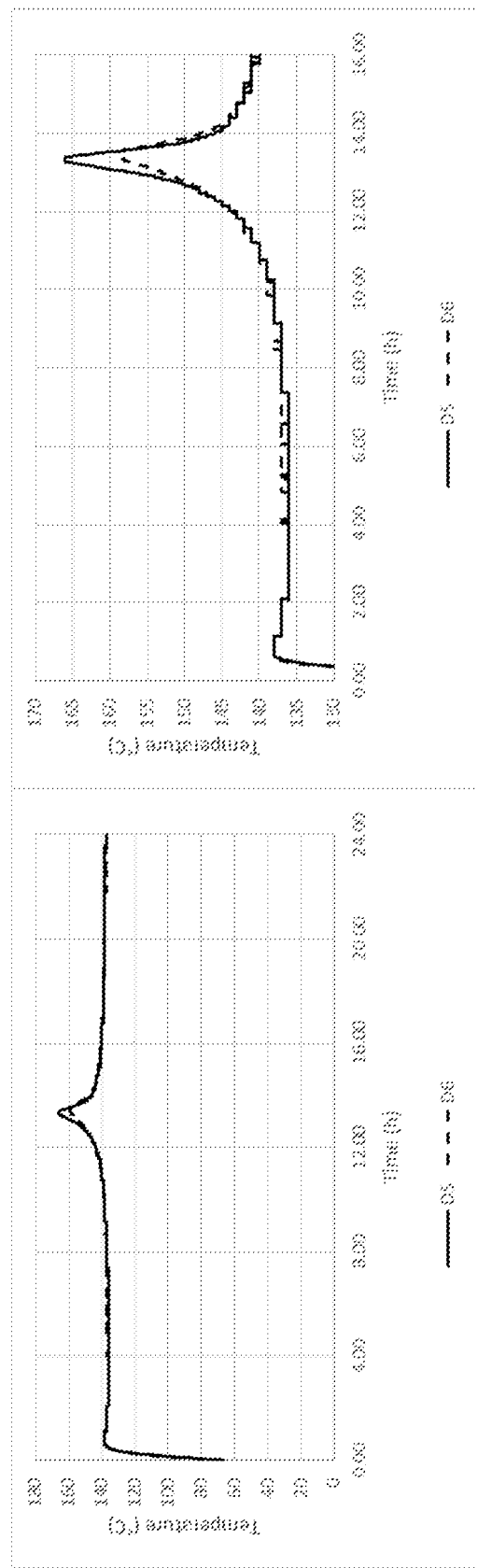
Figure 13:
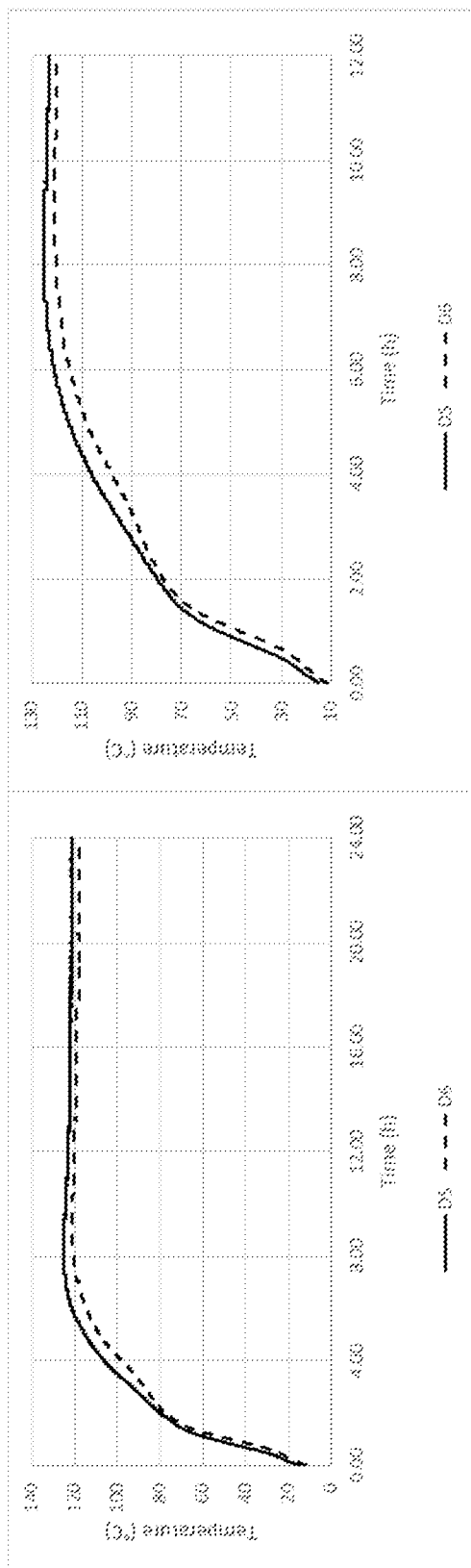

In this example, the same *Schizochytrium* sp. strain as in Example 1 was used. Adding the antioxidant ethoxyquin along with lecithin to pasteurized fermentation broth (D6) helped improve self-heating performance when compared to broth with only ethoxyquin (D5). Both samples were dried via drum drying. See Table 6. Two tests were performed on each of these samples: 25 mm cube at 140° C. and 100 mm cube at 120° C. The temperature profile for each test can be seen in FIG. 12 and FIG. 13. For the 25 mm cube at 140° C., the maximum temperature was 7° C. lower in D6 compared to D5. For the 100 mm cube at 120° C., both samples followed a similar temperature profile, although D6 stayed about 5° C. lower than D5 throughout the entirety of the test. The results of both tests showed that adding lecithin along with ethoxyquin can help reduce the chance of self-heating.

TABLE 6

| Sample | Culture Age (Days) | Pasteurized? | Drying Method | Fat % | PUFA % | Additions |
|---|---|---|---|---|---|---|
| D5 | 6 | Yes | Drum Drying | 51.2% | 47.4% | 2000 ppm ethoxyquin |
| D6 | 6 | Yes | Drum Drying | 49.6% | 47.3% | 2000 ppm ethoxyquin, 1% lecithin |

Example 6

Figure 14:
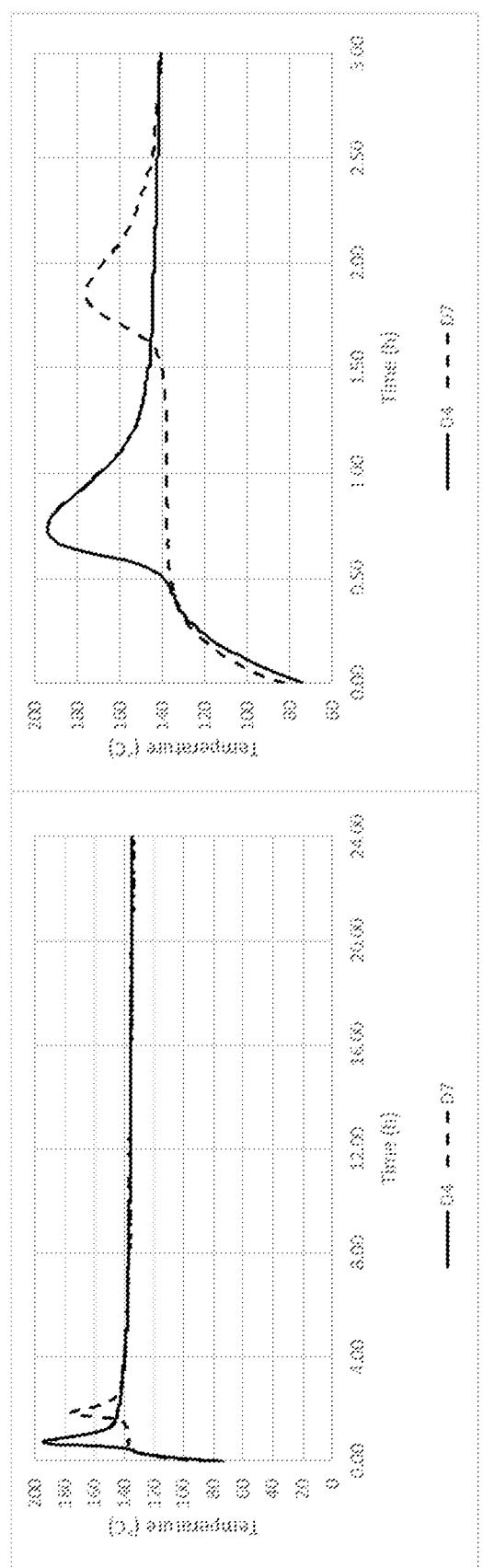
Figure 15:
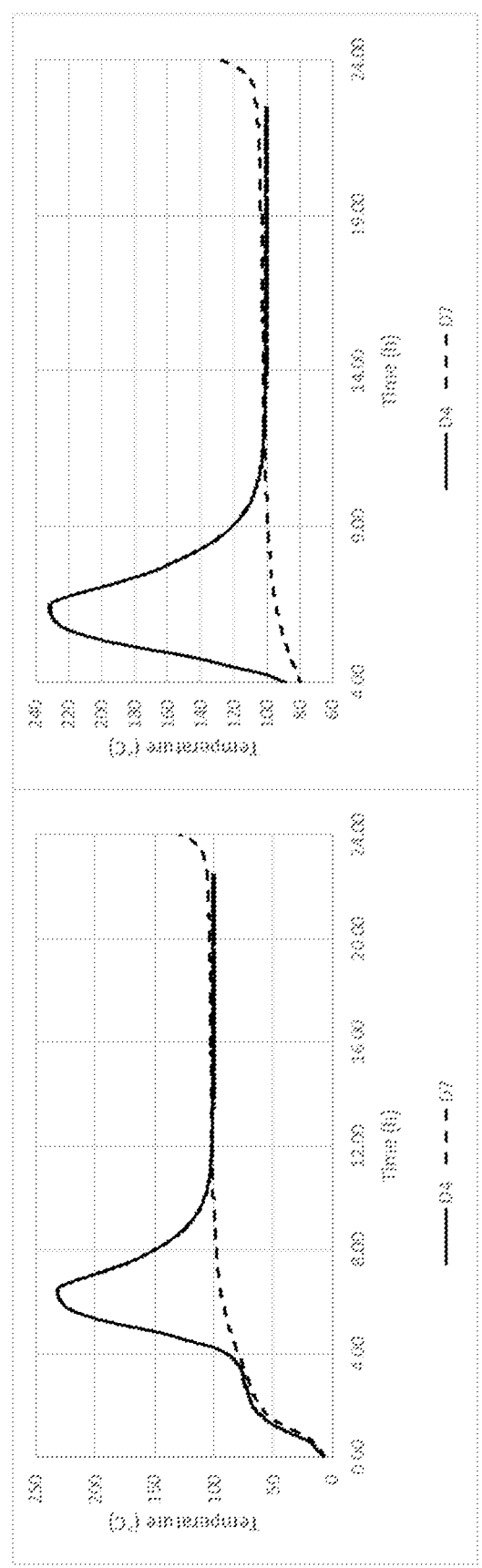

In this example, the same *Schizochytrium* sp. strain as in Example 1 was used. Adding the antioxidant Roseen to pasteurized fermentation broth (D7) helped improve self-heating when compared to broth with no antioxidant (D4). See Table 7. Both samples were dried via drum drying. Two tests were performed on each of these samples: 25 mm cube at 140° C. and 100 mm cube at 100° C. The temperature profile for each test can be seen in FIG. 14 and FIG. 15. For the 25 mm cube at 140° C., the maximum temperature was reduced by 18° C. and the time taken to reach that temperature was increased by 1.1 hours for D7 when compared to D4. For the 100 mm cube at 100° C., D7 did not exhibit self-heating until the end of the testing window, while D4 exhibited dangerous self-heating 6.2 hours into the test. The results of both tests according to FIG. 1, classify D4 in Packing Group III, while D7 would be exempted from packing and labeling under Packing Group III if it is transported in volumes no more than 450 liters.

TABLE 7

| Sample | Culture Age (Days) | Pasteurized? | Drying Method | Fat % | PUFA % | Additions |
|---|---|---|---|---|---|---|
| D4 | 6 | Yes | Drum Drying | 50.6% | 47.4% | None |
| D7 | 6 | Yes | Drum Drying | 52.1% | 46.3% | 2% Roseen |

Example 7

Figure 16:
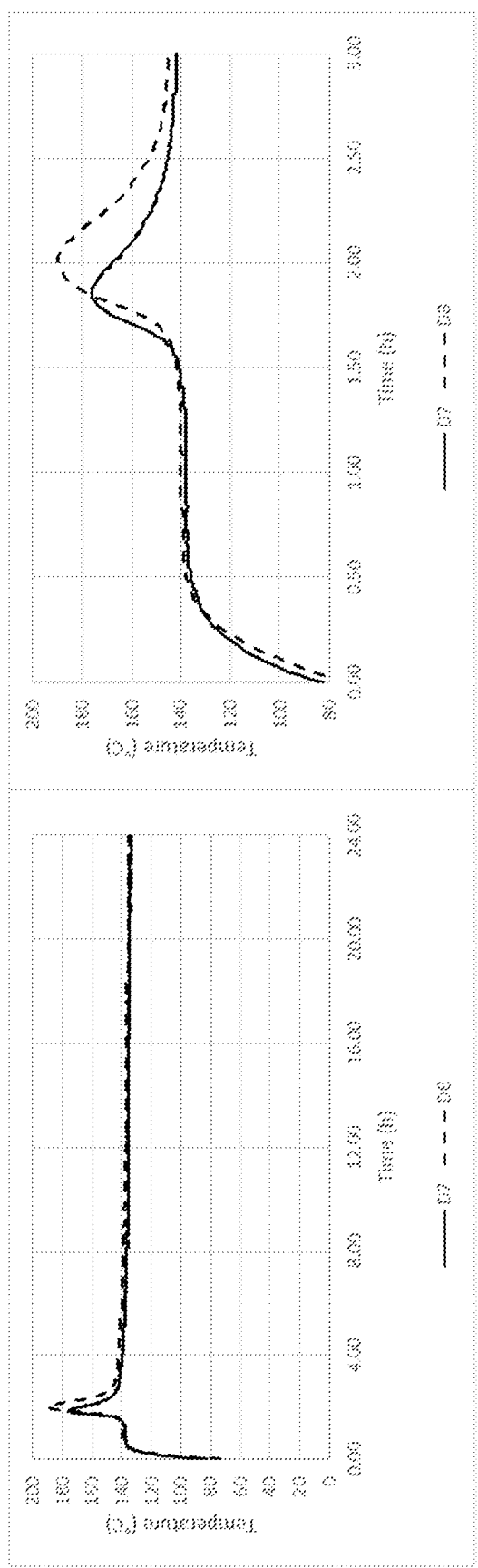
Figure 17:
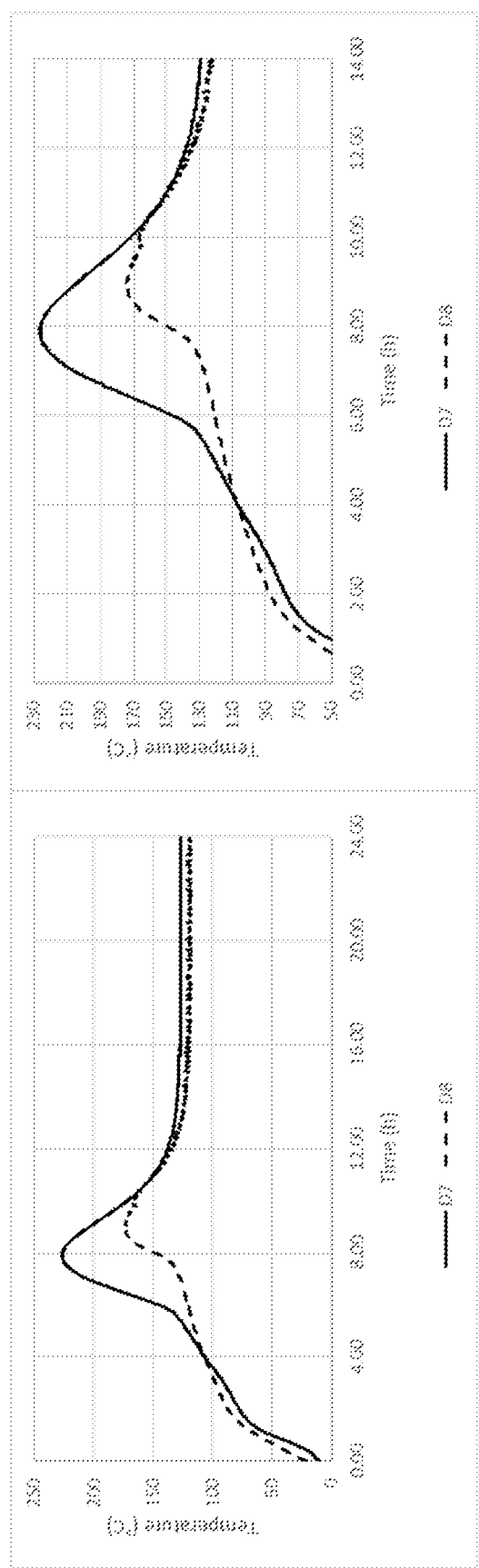

In this example, the same *Schizochytrium* sp. strain as in Example 1 was used. Adding the antioxidant Roseen along with lecithin to pasteurized fermentation broth (D8) helped improve self-heating when compared to broth with only Roseen (D7). Both samples were dried via drum drying. See Table 8. Two tests were performed on each of these samples: 25 mm cube at 140° C. and 100 mm cube at 120° C. The temperature profile for each test can be seen in FIG. 16 and FIG. 17. For the 25 mm cube at 140° C., although the maximum temperature was 14° C. higher for D8 compared to D7, D8 took 0.2 hours longer than D7 to reach that temperature. For the 100 mm cube at 120° C., the maximum temperature was reduced by 52° C. and the time to reach that temperature was increased by 1.1 hours in D8 compared to D7. According to FIG. 1, D7 would be exempted from packing and labeling under Packing Group III if transported in volumes <450 L, while more testing would be needed to classify D8.

TABLE 8

| Sample | Culture Age (Days) | Pasteurized? | Drying Method | Fat % | PUFA % | Additions |
|---|---|---|---|---|---|---|
| D7 | 6 | Yes | Drum Drying | 52.1% | 46.3% | 2% Roseen |
| D8 | 6 | Yes | Drum Drying | 51.6% | 46.1% | 2% Roseen, 1% lecithin |

Example 8

Figure 18:
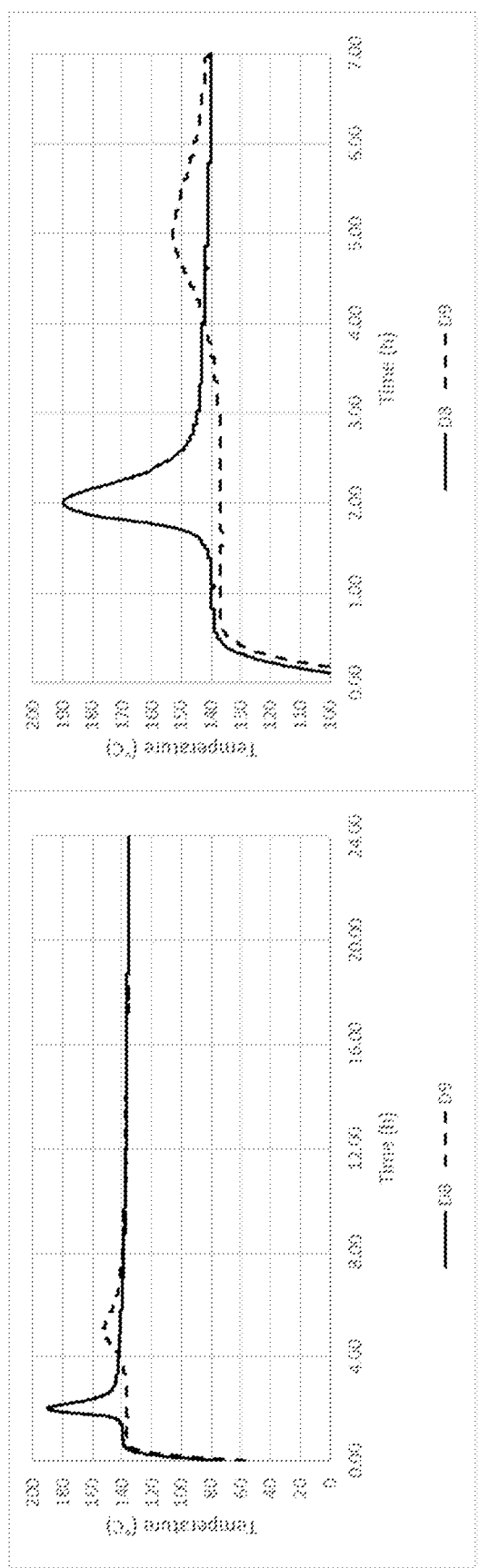
Figure 19:
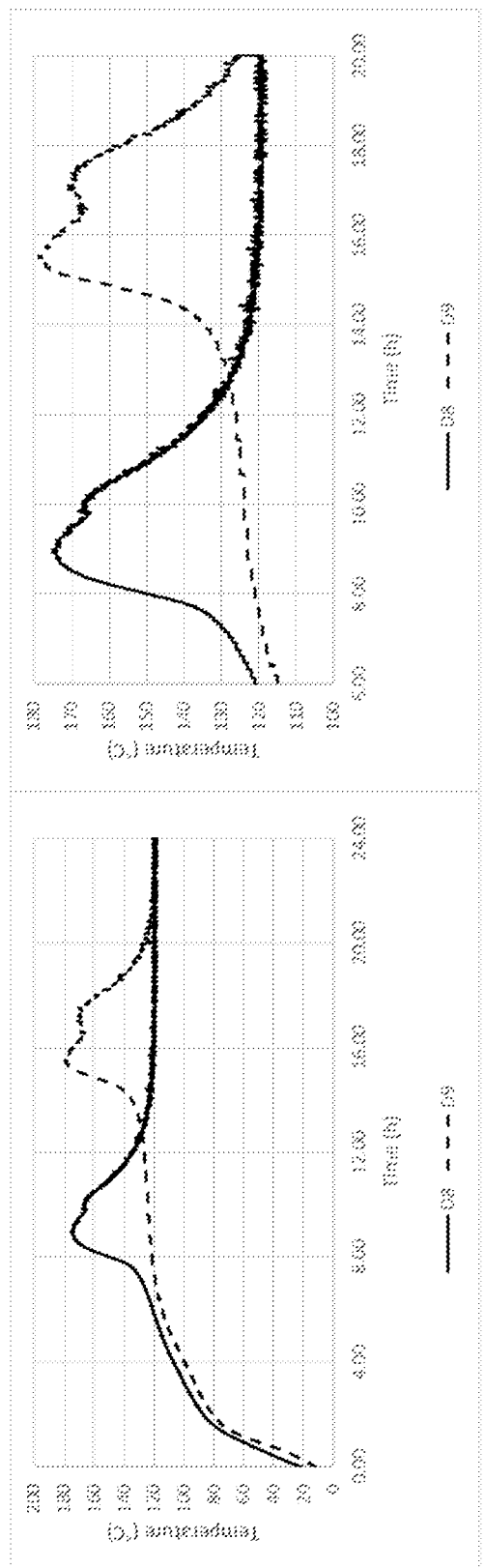

In this example, the same *Schizochytrium* sp. strain as in Example 1 was used. Adding the antioxidants Roseen and TAP1010 along with lecithin to pasteurized fermentation broth (D9) helped improve self-heating when compared to broth with only Roseen and lecithin (D8). Both samples were dried via drum drying. Two tests were performed on each of these samples: 25 mm cube at 140° C. and 100 mm cube at 120° C. The temperature profile for each test can be seen in FIG. 18 and FIG. 19. For the 25 mm cube at 140° C., the maximum temperature was reduced by 37° C. and the time taken to reach that temperature was increased by 3 hours for D9 when compared to D8. For the 100 mm cube at 120° C., although the maximum temperatures reach for both samples were similar, D9 took 6.5 hours longer than D8 to reach that temperature. The results of both tests show that the addition of TAP1010 can further reduce the chance of self-heating.

TABLE 9

| Sample | Culture Age (Days) | Pasteurized? | Drying Method | Fat % | PUFA % | Additions |
|---|---|---|---|---|---|---|
| D8 | 6 | Yes | Drum Drying | 51.6% | 46.1% | 2% Roseen, 1% lecithin |
| D9 | 6 | Yes | Drum Drying | 51.6% | 46.5% | 2% Roseen, 1% lecithin, 4000 ppm TAP1010 |

Example 9

Figure 20:
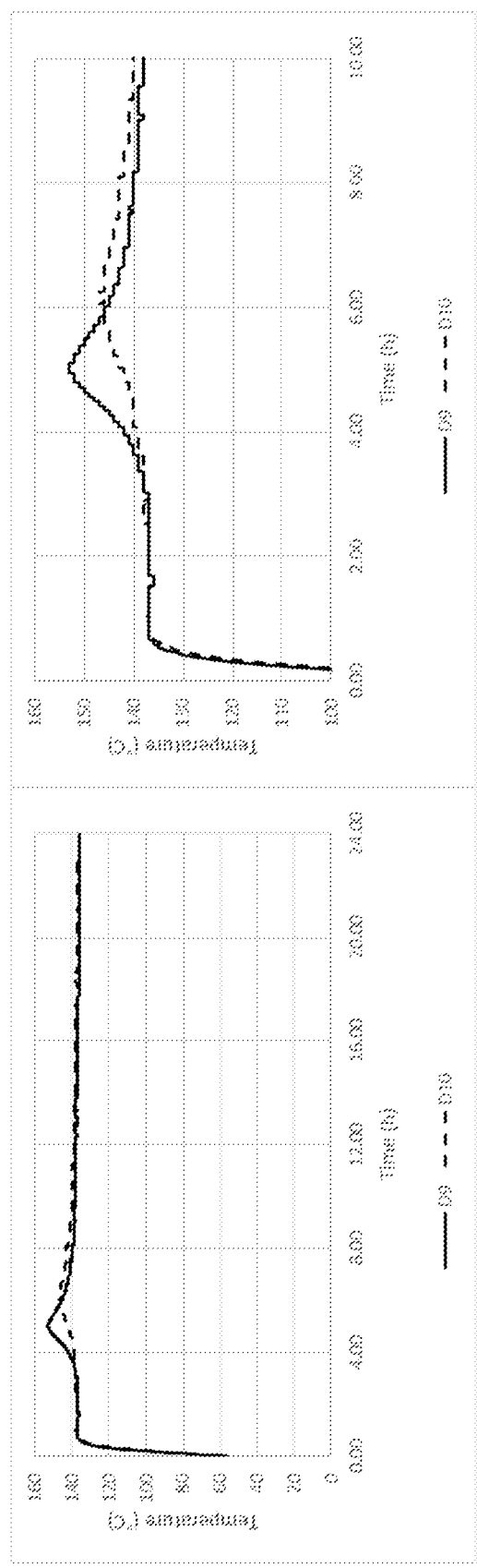
Figure 21:
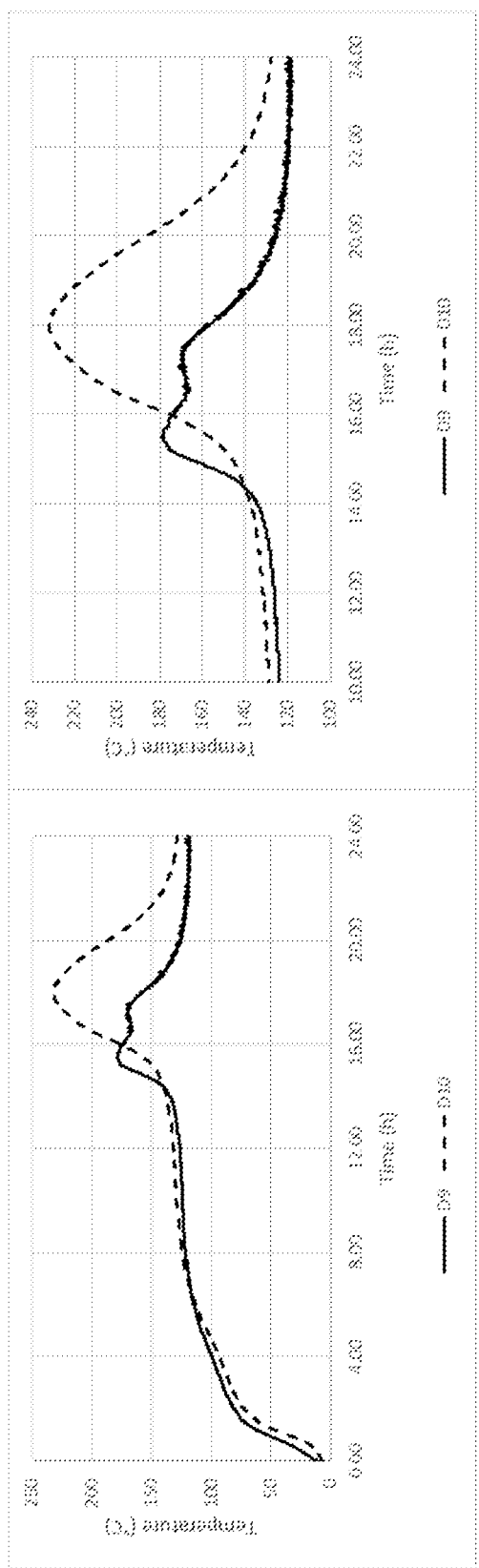

In this example, the same *Schizochytrium* sp. strain as in Example 1 was used. Adding the antioxidants Roseen, TAP1010, and TBHQ along with lecithin to pasteurized fermentation broth (D10) helped improve self-heating when compared to broth with only Roseen, TAP1010, and lecithin (D9). See Table 10. Both samples were dried via drum drying. Two tests were performed on each of these samples: 25 mm cube at 140° C. and 100 mm cube at 120° C. The temperature profile for each test can be seen in FIG. 20 and FIG. 21. For the 25 mm cube at 140° C., the maximum temperature was reduced by 6° C. and the time taken to reach that temperature was increased by 1.1 hours for D10 when compared to D9. For the 100 mm cube at 120° C., although the maximum temperature was 53° C. higher for D10 compared to D9, it took 2.4 hours longer to reach that maximum temperature. The results of both of these tests show that the addition of TBHQ may help delay the onset of self-heating.

TABLE 10

| Sample | Culture Age (Days) | Pasteurized? | Drying Method | Fat % | PUFA % | Additions |
|---|---|---|---|---|---|---|
| D9 | 6 | Yes | Drum Drying | 51.6% | 46.5% | 2% Roseen, 1% lecithin, 4000 ppm TAP1010 |
| D10 | 6 | Yes | Drum Drying | 50.3% | 46.3% | 2% Roseen, 1% lecithin, 4000 ppm TAP1010, 300 ppm TBHQ |

Example 10

Figure 22:
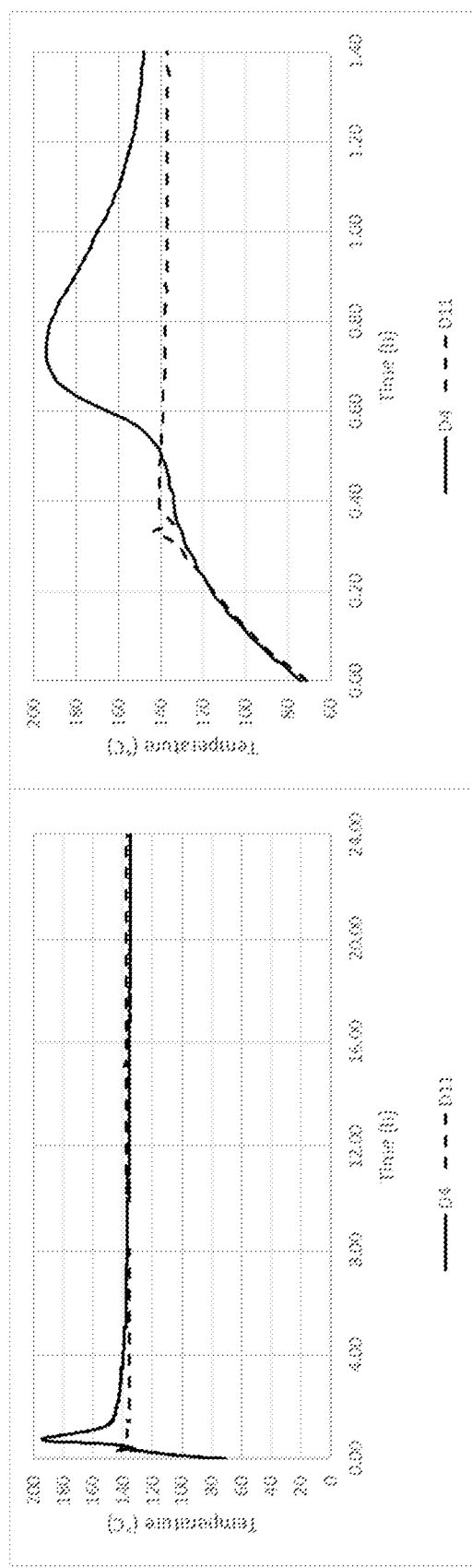
Figure 23:
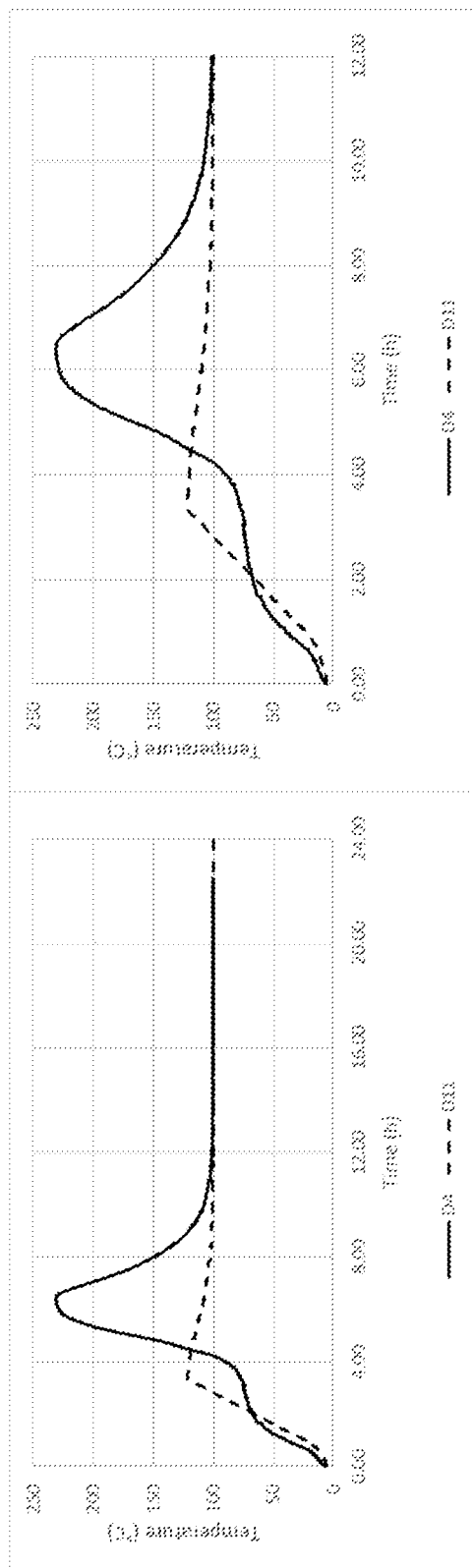

In this example, the same *Schizochytrium* sp. strain as in Example 1 was used. Experiments were also conducted to test the effectiveness of including inert ingredients in biomass. The inclusion of dextrose to pasteurized fermentation broth (D11) helped improve self-heating when compared to broth with low residual glucose (D4). See Table 11. Both samples were dried via drum drying. Two tests were performed on each of these samples: 25 mm cube at 140° C. and 100 mm cube at 100° C. The temperature profile for each test can be seen in FIG. 22 and FIG. 23. For the 25 mm cube at 140° C., although the time taken to reach the maximum temperature was decreased by 0.4 hours, the maximum temperature was reduced by 50° C. for D11 when compared to D4. For the 100 mm cube at 100° C., although the time taken to reach the maximum temperature was decreased by 2.9 hours, the maximum temperature was reduced by 110° C. for D11 when compared to D4. Therefore, D4 would be classified in Packing Group III, and D11 would not be required to be packed and labeled in Packing Group III or Packing Group II according to FIG. 1.

TABLE 11

| Sample | Culture Age (Days) | Pasteurized? | Drying Method | Fat % | PUFA % | Additions |
|---|---|---|---|---|---|---|
| D4 | 6 | Yes | Drum Drying | 50.6% | 47.4% | None |
| D11 | 6 | Yes | Drum Drying | 37.9% | 48.3% | Add 50 g/L dextrose |
| S6 | 6 | Yes | Lyophilization | 48.5% | 48.9% | None |
| S7 | 6 | Yes | Lyophilization | 30.9% | 47.4% | Add 50 g/L fructose |
| S8 | 6 | Yes | Lyophilization | 37.9% | 47.8% | Add 50 g/L sucrose |
| S9 | 6 | Yes | Lyophilization | 37.8% | 48.7% | Add 50 g/L maltose |

Figure 24:
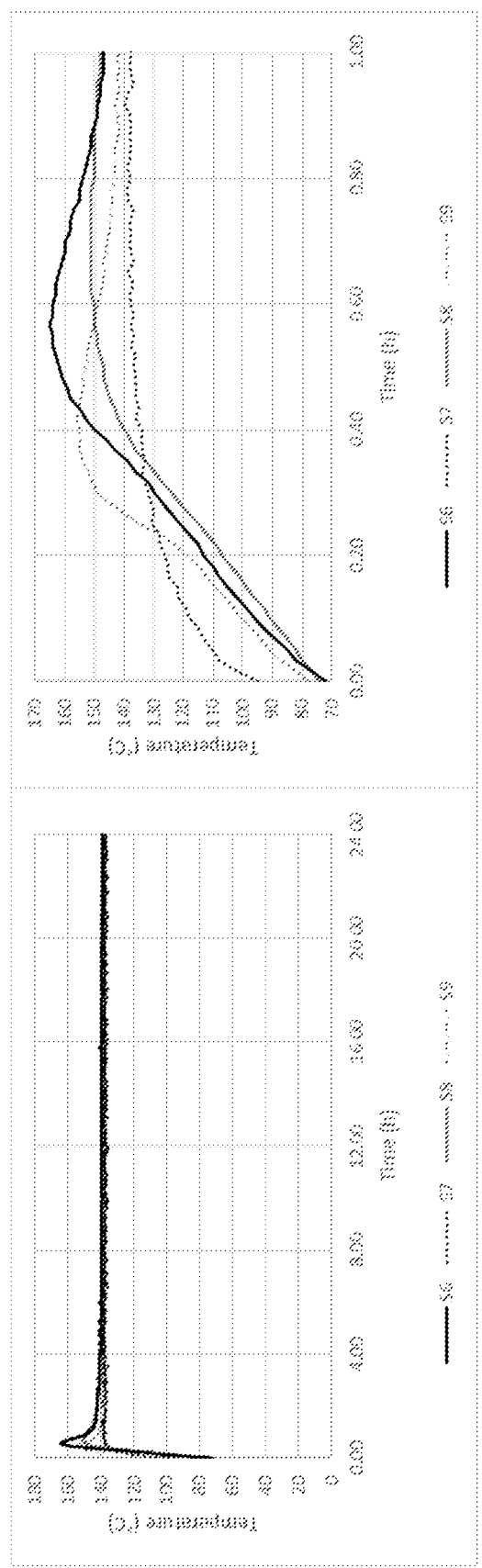
Figure 25:
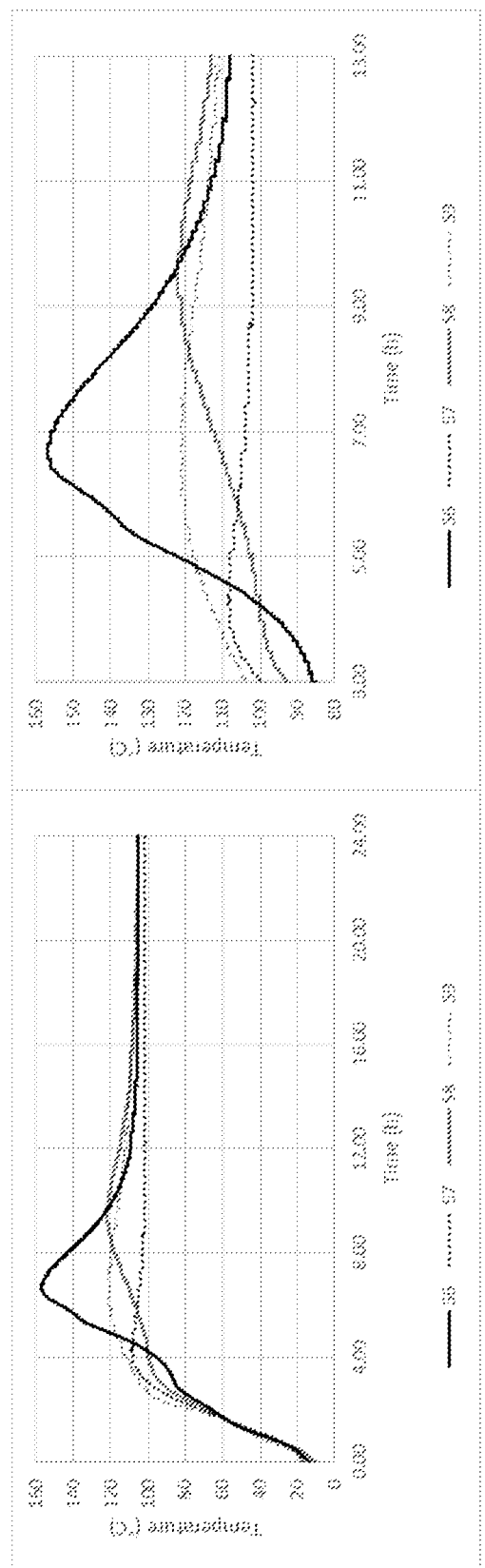

Experiments were then conducted using the addition of different sugars (fructose, sucrose, and maltose). The addition of these sugars to pasteurized fermentation broth (S7-9) helped improve self-heating when compared to broth with low residual glucose (S6). These samples were all dried via lyophilization. Two tests were performed on each of these samples: 25 mm cube at 140° C. and 100 mm cube at 100° C. The temperature profile for each test can be seen in FIG. 24 and FIG. 25. For the 25 mm cube at 140° C., all samples containing sugar (S7-9) reached a lower maximum temperature than the control (S6). Each sugar, though, decreased the temperature by different amounts: fructose (S7)-24° C., sucrose (S8)-14° C., and maltose (S9)-9° C. Similarly, for the 100 mm cube at 100° C., all samples containing sugar (S7-9) reached a lower maximum temperature than the control (S6). For the sample containing fructose (S7), the maximum temperature was 48° C. below the control, but reached this temperature about two hours faster. For the sample containing sucrose (S8), the maximum temperature was 35° C. below the control and it took 2.5 hours longer to reach that temperature. For the sample containing maltose (S9), the maximum temperature was 36° C. below the control, but it reached this temperature about 0.6 hours faster. Therefore, sugars within the fermentation broth can help reduce self-heating characteristics. The presence of sugars can be achieved either through addition of the sugars to a completed fermentation or through residual amounts; where the fermentation is completed before all sugars from feedstock(s) are consumed.

Example 11

Figure 26:
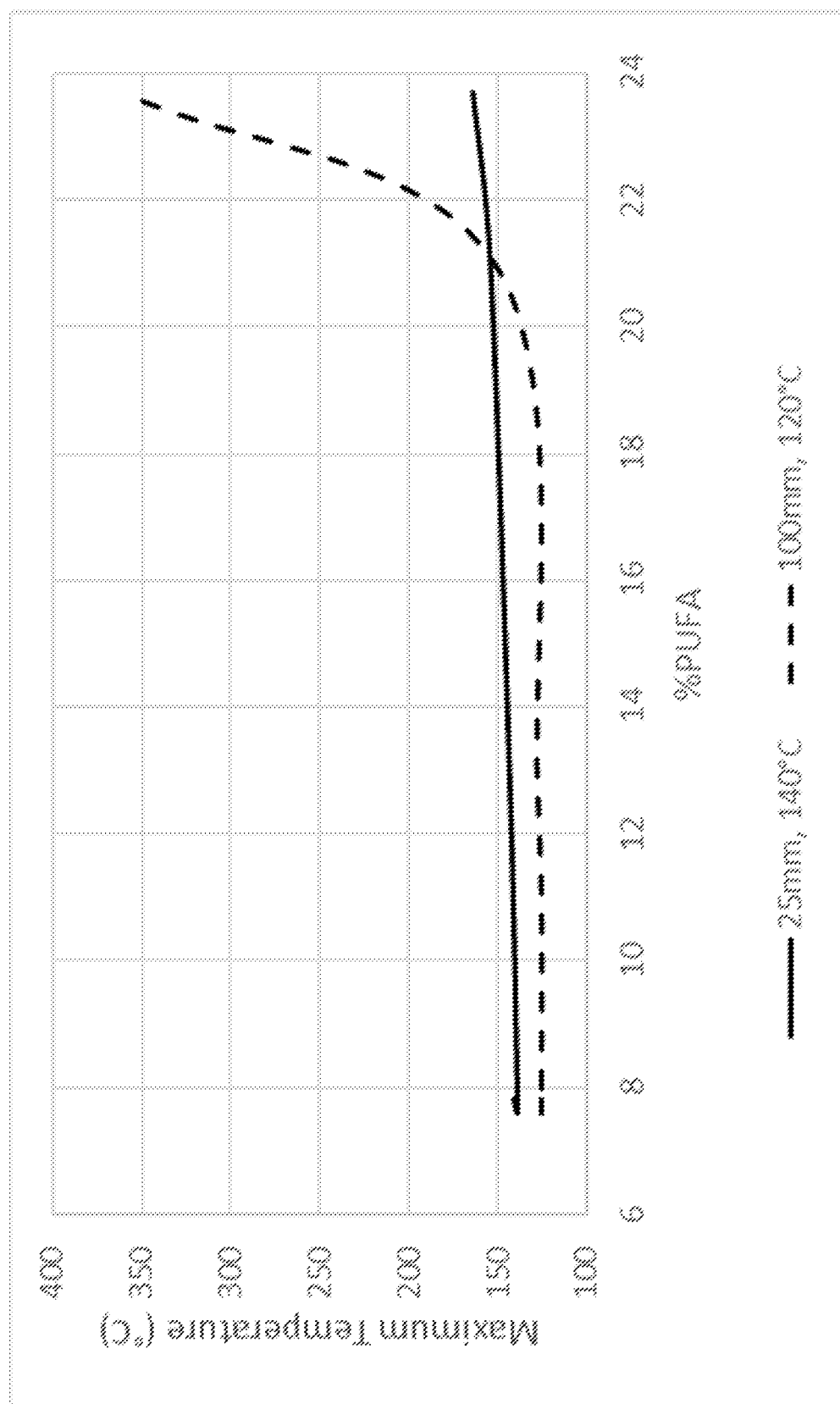
FIG. 26 shows the maximum temperature reached for samples with various PUFA percentages in a 25 mm cube at 140° C. and a 100 mm cube at 120° C.

In this example, the same *Schizochytrium* sp. strain as in Example 1 was used. Harvesting fermentation broth at different time points resulted in dry samples with various amounts of PUFA (polyunsaturated fat) with the earlier samples having the least PUFA and the later samples having the most. See Table 12. The PUFA percent in the samples S1-S5 (previously discussed in example 1) was plotted against the maximum temperature the sample reached during the oven test (25 mm cube at 140° C. and 100 mm cube at 120° C.) in the graph below (FIG. 26). For the 25 mm cube at 140° C., the maximum temperature reached only increased slightly with the increase in PUFA percent. For the 100 mm cube at 120° C., though, the maximum temperature reached greatly increased when the PUFA percent in the biomass went over 20%. Therefore, keeping the PUFA percent of the dry biomass below 20% can help reduce product self-heating.

TABLE 12

| Sample | Pasteurized? | Drying Method | Fat % | PUFA % in Fat | PUFA% in Biomass |
|---|---|---|---|---|---|
| S1 | No | Lyophilization | 14.1% | 49.6% | 6.9% |
| S2 | No | Lyophilization | 14.9% | 45.0% | 6.7% |
| S3 | No | Lyophilization | 26.6% | 42.1% | 11.2% |
| S4 | No | Lyophilization | 41.3% | 45.3% | 18.7% |
| S5 | No | Lyophilization | 47.3% | 45.2% | 21.4% |

What is claimed is:

1. A PUFA-containing composition comprising:
   a fermented biomass of cells comprising at least 20 wt % of at least one type of polyunsaturated fatty acid (PUFA) having at least 20 carbon atoms and at least three double bonds, wherein
   the PUFA-containing composition has a reduced self-heating propensity sufficient to cause a temperature of the PUFA-containing composition to not spontaneously be increased to 180° C. or more in an oven when the PUFA-containing composition is placed in a 100 mm sample cube and is heated in the oven at 120° C. for 24 hours,
   wherein the reduced self-heating propensity is obtained by:
   (i) limiting fermentation of the biomass to less than 6 days,
   (ii) omitting a pasteurization step after fermentation,
   (iii) conducting a drum drying step instead of a lyophilzation step,
   (iv) adding at least one type of natural antioxidant and at least one type of synthetic antioxidant to a fermentation broth at the end of fermentation, or
   (v) including at least 50 g/L sugar to a fermentation broth at the end of fermentation.

2. The PUFA-containing composition according to claim 1, wherein the composition comprises at least 25 wt % of the at least one PUFA.

3. The PUFA-containing composition according to claim 1, wherein the composition comprises at least 30 wt % of the at least one PUFA.

4. The PUFA-containing composition according to claim 1, wherein the composition comprises at least 40 wt % of the at least one PUFA.

5. The PUFA-containing composition according to claim 1, wherein the composition comprises at least 50 wt % of the at least one PUFA.

6. The PUFA-containing composition according to claim 1, wherein the at least one PUFA is an ω-3 PUFA or an ω-6 PUFA.

7. The PUFA-containing composition according to claim 6, wherein the cells are microbial cells.

8. The PUFA-containing composition according to claim 7, wherein the microbial cells are of the genus *Mortierella, Schizochytrium, Thraustochytrium* or *Crypthecodinium*.

9. The PUFA-containing composition according to claim 1, wherein the fermented biomass comprises at least one microbial oil, wherein the at least one microbial oil further comprises an effective amount of at least one added antioxidant to provide oxidative stability.

* * * * *